(12) United States Patent  
Okada et al.

(10) Patent No.: US 8,625,186 B2  
(45) Date of Patent: Jan. 7, 2014

(54) ELECTROCHROMIC COMPOUND, ELECTROCHROMIC COMPOSITION, AND DISPLAY DEVICE

(71) Applicants: Takashi Okada, Kanagawa (JP); Shigenobu Hirano, Kanagawa (JP); Tsutomu Sato, Kanagawa (JP)

(72) Inventors: Takashi Okada, Kanagawa (JP); Shigenobu Hirano, Kanagawa (JP); Tsutomu Sato, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 13/676,423

(22) Filed: Nov. 14, 2012

(65) Prior Publication Data

US 2013/0135703 A1    May 30, 2013

(30) Foreign Application Priority Data

Nov. 28, 2011  (JP) ................. 2011-259245  
Aug. 23, 2012  (JP) ................. 2012-184228

(51) Int. Cl.  
*G02F 1/15* (2006.01)  
*G02F 1/153* (2006.01)

(52) U.S. Cl.  
USPC .................... 359/265; 359/269; 359/270

(58) Field of Classification Search  
USPC ................................. 359/265–275  
See application file for complete search history.

(56) References Cited

U.S. PATENT DOCUMENTS

| | | | |
|---|---|---|---|
| 6,301,038 B1 | 10/2001 | Fitzmaurice et al. | |
| 2002/0167480 A1 | 11/2002 | Johnson et al. | |

(Continued)

FOREIGN PATENT DOCUMENTS

| | | |
|---|---|---|
| JP | 2001-510590 | 7/2001 |
| JP | 2003-121883 | 4/2003 |

(Continued)

OTHER PUBLICATIONS

D. Witker et al., "Soluble Variable Color Carbazole-Containing Electrochromic Polymers", Macromolecules, 2005, 7636-7644, 38.

(Continued)

*Primary Examiner* — Jack Dinh  
(74) *Attorney, Agent, or Firm* — Cooper & Dunham LLP

(57) ABSTRACT

An electrochromic compound represented by the following General Formula (1)

GENERAL FORMULA (1)

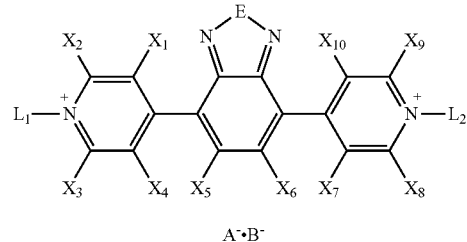

wherein E represents at least one of O, S, Se, and N—R; R represents at least one of a hydrogen atom, a substitutive aliphatic hydrocarbon group, and a substitutive aromatic hydrocarbon group; $X_1$-$X_{10}$ may be the same or different and each represent at least one of a hydrogen atom and a monovalent substituent; $L_1$ and $L_2$ may be the same or different and each represent a monovalent substituent; and $A^-$ and $B^-$ may be the same or different and each represent a monovalent anion.

7 Claims, 7 Drawing Sheets

(56) References Cited

U.S. PATENT DOCUMENTS

| | | |
|---|---|---|
| 2003/0035198 A1 | 2/2003 | Liang et al. |
| 2005/0012977 A1 | 1/2005 | Mizuno |
| 2005/0084711 A1 | 4/2005 | Sasaki et al. |
| 2006/0247413 A1 | 11/2006 | Sasaki et al. |
| 2007/0048637 A1 | 3/2007 | Okada et al. |
| 2007/0092760 A1 | 4/2007 | Sagisaka et al. |
| 2007/0213503 A1 | 9/2007 | Sasaki et al. |
| 2008/0013152 A1 | 1/2008 | Hirano et al. |
| 2008/0112033 A1 | 5/2008 | Shibuya et al. |
| 2009/0230386 A1 | 9/2009 | Yamamoto et al. |
| 2010/0219405 A1 | 9/2010 | Sagisaka et al. |
| 2010/0298527 A1 | 11/2010 | Beaujuge et al. |
| 2011/0040107 A1 | 2/2011 | Goto et al. |
| 2012/0035364 A1 | 2/2012 | Shinoda et al. |
| 2012/0065353 A1 | 3/2012 | Sasaki et al. |
| 2012/0119195 A1 | 5/2012 | Sagisaka et al. |
| 2012/0194894 A1 | 8/2012 | Yashiro et al. |

FOREIGN PATENT DOCUMENTS

| | | |
|---|---|---|
| JP | 2003-161964 | 6/2003 |
| JP | 2003-270671 | 9/2003 |
| JP | 2004-151265 | 5/2004 |
| JP | 2004-520621 | 7/2004 |
| JP | 2004-361514 | 12/2004 |
| JP | 2004-536344 | 12/2004 |
| JP | 2006-106669 | 4/2006 |
| JP | 2008-122578 | 5/2008 |
| JP | 2010-145814 | 7/2010 |
| JP | 2011-503260 | 1/2011 |
| JP | 2011-102287 | 5/2011 |

OTHER PUBLICATIONS

European Search Report dated Jan. 28, 2013 in connection with counterpart European patent application No. 12 19 3127.3.

G. Qian et al., "A precursor strategy for the synthesis of low band-gap polymers: an efficient route to a series of near-infrared electrochromic polymers", J. Mater. Chem., 2011, 7678, 21.

E. Kaya et al., "Electrochromic and optical studies of solution processable benzotriazole and fluorene containing copolymers", Organic Electronics, 2011, 202-209, 12.

D. Witker et al., "Soluble Variable Color Carbazole-Containing Electrochromic Polymers", Macromolecules, 2005 7636-7644, 38.

ELECTROCHROMIC COMPOUND, ELECTROCHROMIC COMPOSITION, AND DISPLAY DEVICE

BACKGROUND OF THE INVENTION

1. Field of the Invention

The disclosures herein generally relate to an electrochromic compound, an electrochromic composition, and a display device.

2. Description of the Related Art

Recently, efforts are being directed to developing electronic paper as an electronic medium to be used in place of paper. The electronic paper may be embodied by a display device that is designed to be used just like ordinary paper. Such a display device desirably has characteristics that are different from those of traditional display devices such as a CRT (Cathode Ray Tube) or an LCD (Liquid Crystal Display). For example, the electronic paper may require a display device to have the characteristics of a reflective display, to have a high white reflectivity and a high contrast ratio, to display high-resolution images, to have an adequate memory effect, to operate even with a low voltage input, to be thin and light-weight, and to be inexpensive. The electronic paper has particularly demanding requirements with regard to color display characteristics and display quality characteristics such as having the same white reflectivity and contrast ratio as those of paper.

There have been disclosures related to display techniques adopted by a display device for the electronic paper including a method of using a reflective liquid crystal, a method of using electrophoresis, and a method of using toner migration, for example. However, it is difficult to display multiple colors while maintaining a high white reflectivity and a high contrast ratio when using the above disclosed techniques. To display multiple colors, a color filter is conventionally used. The color filter, however, may absorb light, and as a result, the reflectivity of the display device may be reduced. Also, by using the color filter, one pixel is divided into three regions (i.e., red (R), green (G), and blue (B) regions). Therefore, the reflectivity of the display device may be reduced and the contrast ratio may be reduced accordingly. When the white reflectivity and the contrast ratio are greatly reduced, the visibility may also be degraded. As a result, it may be difficult to use the display device as electronic paper.

Japanese Laid-Open Patent Publication Nos. 2003-161964 and 2004-361514 (Patent Documents 1-2) disclose techniques related to a reflective color display medium having a color filter arranged on an electrophoresis element. However, a desirable image cannot be obtained even if a color filter is arranged on a display medium with a low reflectivity and a low contrast ratio.

Japanese Translation of PCT International Application Publication Nos. 2004-520621 and 2004-536344 (Patent Documents 3-4) disclose techniques related to an electrophoresis element that enables color display by moving particles that are in plural different colors. However, these techniques cannot fundamentally resolve the above-described problem related to the demand for a high reflectivity and a high contrast ratio. That is, the above techniques cannot achieve a high white reflectivity and a high contrast ratio at the same time.

On the other hand, there is one promising technique for the reflective display device using an electrochromic phenomenon without using a color filter. The electrochromic phenomenon is also called electrochromism and refers to a phenomenon in which electrochromic materials applied with a voltage show a reversible color change during an electrochemical redox reaction. An electrochromic display device, which utilizes such a color change (i.e., coloration and decoloration) in the electrochromic materials that cause such a phenomenon, has emerged as a candidate for electrochromic paper because it serves as a reflective display device, has high white reflectivity as well as a memory effect, and can be driven at a low voltage.

It is noted that since the electrochromic display device utilizes the coloration/decoloration during redox reactions, the coloration/decoloration response speed of the electrochromic display device may be relatively slow. In turn, for example, Japanese Translation of PCT International Application Publication No. 2001-510590 (Patent Document 5) discloses a technique for improving the coloration/decoloration response speed by fixing (disposing) an electrochromic compound near an electrode. This document describes how the coloration/decoloration time which conventionally took a few dozen seconds can be reduced such that both the coloration time from colorless to blue and the decoloration time from blue to colorless may only take about 1 second. However, the improvement in the coloration/decoloration response speed realized by the above technique is not adequate and further improvements in the coloration/decoloration response speed are in demand.

The electrochromic display device may display various colors depending on the structure of the electrochromic compound and may be reversibly changed from a decolored state to a colored state. Thus, the electrochromic display device may be capable of multicolor display using a layered structure. By realizing multicolor display using a layered structure, degradation of the reflectivity and the contrast ratio of the display device may be prevented since one pixel would not have to be divided into three regions (i.e., red (R), green (G), and blue (B) regions) as in the conventional display device.

For example, Japanese Laid-Open Patent Publication No. 2003-121883 (Patent Document 6) discloses a multicolor electrochromic display device that has plural types of electrochromic compound particles arranged into layers. The disclosed multicolor electrochromic display device arranges multiple layers of electrochromic compounds corresponding to high polymer compounds having plural functional groups that produce color at differing voltages.

Additionally, Japanese Laid-Open Patent Publication No. 2006-106669 (Patent Document 7) discloses a multicolor display device having plural electrochromic layers arranged on an electrode, the device being configured to produce multiple colors by utilizing the differences in the voltages and electric currents required for causing coloration of the electrochromic layers. The disclosed multicolor display device includes a display layer formed by layering or mixing two or more of electrochromic compositions that develop different colors, have different threshold voltages for coloration, and require different charge amounts for achieving coloration to a sufficient color density.

Further, Japanese Laid-Open Patent Publication No. 2003-270671 (Patent Document 8) discloses a multicolor display device that has plural layers of a structural unit that is formed by arranging an electrochromic layer and an electrolyte between a pair of transparent electrodes. Japanese Laid-Open Patent Publication No. 2004-151265 (Patent Document 9) discloses a multicolor display device that uses the above structural unit to form a passive matrix panel and an active matrix panel to realize multicolor display according to the RGB color model.

The electrochromic display devices disclosed in Patent Documents 5-7 use viologen organic electrochromic compounds that are capable of developing colors such as blue and green but are not capable of developing the three primary colors, yellow (Y), magenta (M), and cyan (C) that are required for realizing full-color display.

Japanese Laid-Open Patent Publication Nos. 2008-122578 and 2011-102287 (Patent Documents 10-11) disclose the use of styryl dye to enable YMC coloration. The electrochromic display devices disclosed in Patent Documents 8-9 also use the styryl dye to enable YMC coloration.

The electrochromic display devices disclosed in Patent Documents 5-11 have problems related to coloration stability and fall short of achieving desired characteristics as an electrochromic display device. For example, in the disclosed electrochromic display devices, the memory effect is inadequate and when an applied voltage is turned off, color that has been gradually developing may disappear relatively fast.

SUMMARY OF THE INVENTION

It is a general object of at least one embodiment of the present invention to provide an electrochromic compound that substantially obviates one or more problems caused by the limitations and disadvantages of the related art.

In one embodiment, an electrochromic compound is represented by the following General Formula (1)

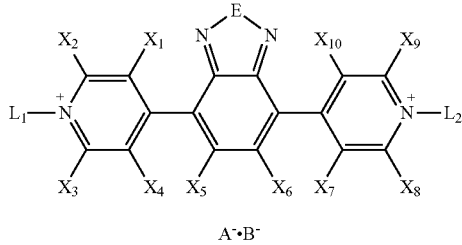

GENERAL FORMULA (1)

wherein E represents at least one of O, S, Se, and N—R; R represents at least one of a hydrogen atom, a substitutive aliphatic hydrocarbon group, and a substitutive aromatic hydrocarbon group; $X_1$-$X_{10}$ may be the same or different and each represent at least one of a hydrogen atom and a monovalent substituent; $L_1$ and $L_2$ may be the same or different and each represent a monovalent substituent; and $A^-$ and $B^-$ may be the same or different and each represent a monovalent anion.

According to an aspect of the present invention, an electrochromic compound, an electrochromic composition, and an electrochromic display device may be provided that have high image maintaining capabilities for maintaining an image density even after an applied voltage is turned off.

BRIEF DESCRIPTION OF THE DRAWINGS

Other objects and further features of embodiments will be apparent from the following detailed description when read in conjunction with the accompanying drawings, in which.

DESCRIPTION OF THE PREFERRED EMBODIMENTS

Figure 1A:
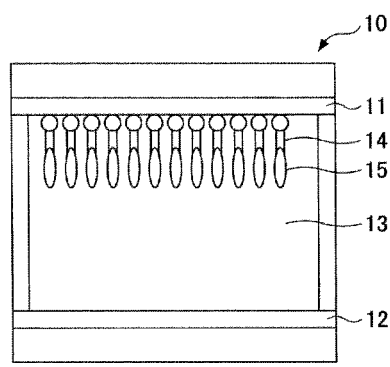
FIGS. 1A and 1B show exemplary configurations of display devices according to a second embodiment of the present invention.

In the following, embodiments of the present invention are described with reference to the accompanying drawings. It is noted that identical features and components are given the same reference numerals and their descriptions may be omitted.

[First Embodiment]

In the following an electrochromic compound and an electrochromic composition according to a first embodiment of the present invention are described.

(Electrochromic Compound)

The electrochromic compound according to the present embodiment is represented by the following General Formula (1).

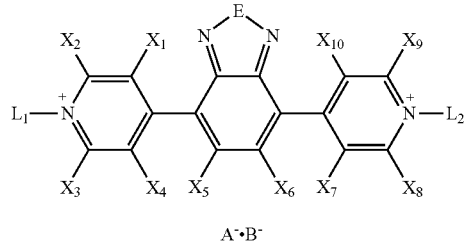

GENERAL FORMULA (1)

In General Formula (1), E represents O, S, Se, or N—R; R represents a hydrogen atom, a substitutive aliphatic hydrocarbon group, or a substitutive aromatic hydrocarbon group; $X_1$-$X_{10}$ may be the same or different and each represent a hydrogen atom or a monovalent substituent; $L_1$ and $L_2$ may be the same or different and each represent a monovalent substituent; and $A^-$ and $B^-$ may be the same or different and each represent a monovalent anion.

Examples of $X_1$-$X_{10}$ include a hydrogen atom, a halogen atom, a hydroxyl group, a nitro group, a cyano group, a carboxyl group, an alkoxycarbonyl group that may include a substituent, an aryloxycarbonyl group that may include a substituent, an alkylcarbonyl group that may include a substituent, an arylcarbonyl group that may include a substituent, an amide group, a monoalkylaminocarbonyl group that may include a substituent, a dialkylaminocarbonyl group that may include a substituent, a monoarylaminocarbonyl group that may include a substituent, a diarylaminocarbonyl group that may include a substituent, a sulfonate group, an alkoxysulfonyl group that may include a substituent, an aryloxysulfonyl group that may include a substituent, an alkylsulfonyl group that may include a substituent, an arylsulfonylamino group that may include a substituent, a sulfonamide group, a monoalkylaminosulfonyl group that may include a substituent, a dialkylaminosulfonyl group that may include a substituent, a monoarylaminosulfonyl group that may include a substituent, a diarylaminosulfonyl group that may include a substituent, an amino group, a monoalkylamino group that may include a substituent, a dialkylamino group that may include a substituent, an alkyl group that may include a substituent, an alkenyl group that may include a substituent, an alkynyl group that may include a substituent, an aryl group that may include a substituent, an alkoxy group that may include a substituent, an aryloxy group that may include a substituent, an alkylthio group that may include a substituent, an arylthio group that may include a substituent, or a heterocyclic group that may include a substituent.

The atoms or groups represented by $X_1$-$X_{10}$ may provide solubility for the solvent of the electrochromic compound so that the display device manufacturing process may be facilitated. Also, these atoms or groups enable adjustment of the coloration spectrum (color). It is noted that these atoms or groups may cause destabilization of the thermal resistance and/or light resistance properties of the electrochromic compound so that in a preferred embodiment, a hydrogen atom, halogen, or a substituent with no more than 6 carbon atoms are used.

Examples of $L_1$ and $L_2$ include an alkyl group that may include a substituent, an alkenyl group that may include a substituent, an alkynyl group that may include a substituent, or an aryl group that may include a substituent. In one preferred embodiment, at least one of $L_1$ and $L_2$ may be a functional group that is capable of directly or indirectly bonding with a hydroxyl group.

The functional group that is capable of directly or indirectly bonding with a hydroxyl group may be any functional group that directly or indirectly bonds with a hydroxyl group through hydrogen bonding, adsorption, or a chemical reaction, for example. Preferred examples of such a functional group include a phosphonate group, a phosphate group, a carboxyl group, a trichlorosilyl group, a trialkoxysilyl group, a monochlorosilyl group, and a monoalkoxysilyl group. Further, preferred examples of the trialkoxysilyl group include a triethoxysilyl group and a trimethoxysilyl group. Of these exemplary functional groups, the trialkoxysilyl group and the phosphonate group that have strong bonding properties for bonding with a conductive or semi-conductive nanostructure are particularly preferred.

$A^-$ and $B^-$ each represent a monovalent anion that may be stably paired with a cation. Although not limited to a particular type of ion, preferred examples of $A^-$ and $B^-$ include Br ions, Cl ions, $ClO_4$ ions, $PF_6$ ions, $BF_4$ ions, and $CF_3SO_3$ ions. In one preferred embodiment, $A^-$ and $B^-$ are the same and represent Br ions, Cl ions, or $ClO_4$ ions.

In the electrochromic compound according to one preferred embodiment, $X_1$-$X_{10}$ are arranged to realize a symmetrical structure to facilitate synthesis and ensure stability.

Although the electrochromic compound according to the present embodiment represented by General Formula (1) is not structurally limited, Formulas (2)-(42) shown below represent exemplary structures of the electrochromic compound according to the present embodiment.

FORMULA (2)

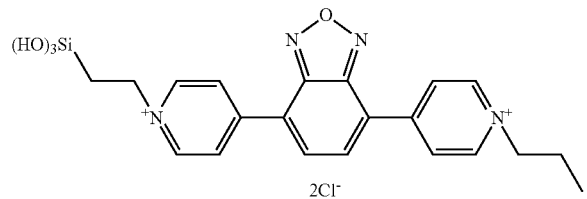

FORMULA (3)

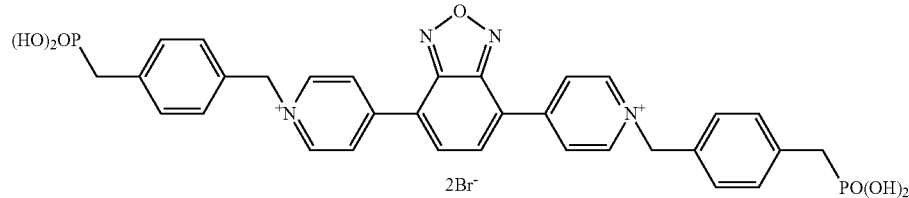

FORMULA (4)

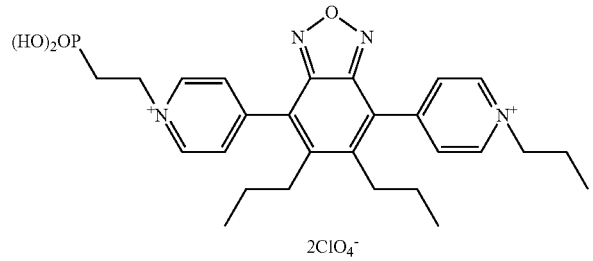

-continued
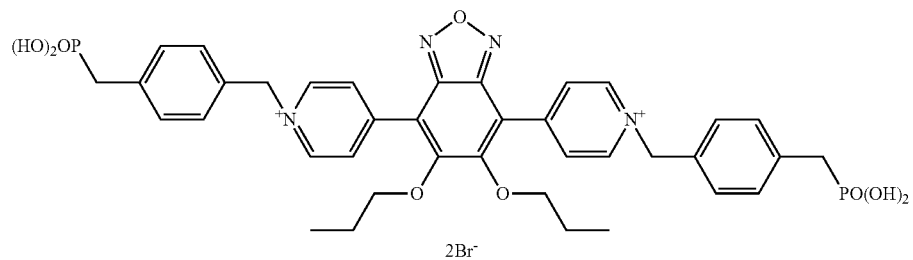
FORMULA (5)
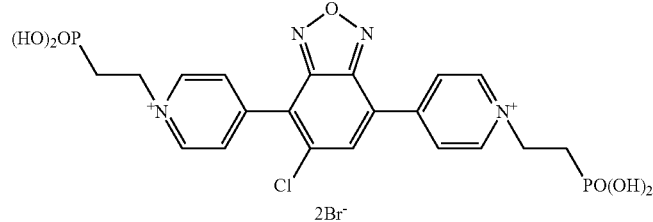
FORMULA (6)
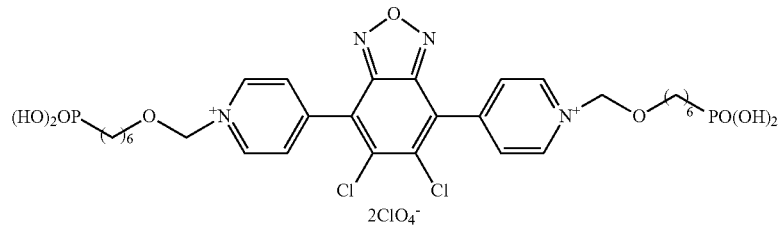
FORMULA (7)
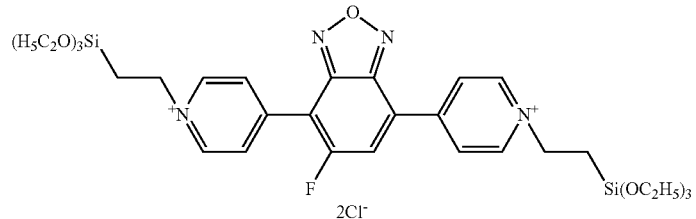
FORMULA (8)
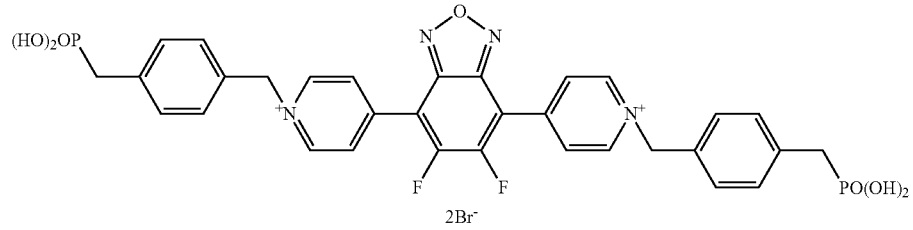
FORMULA (9)
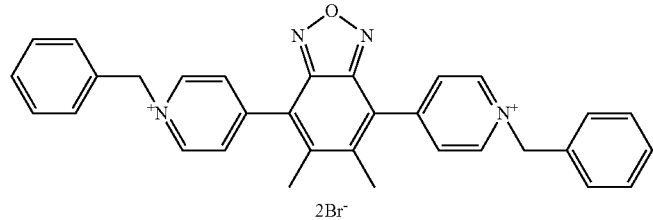
FORMULA (10)

-continued
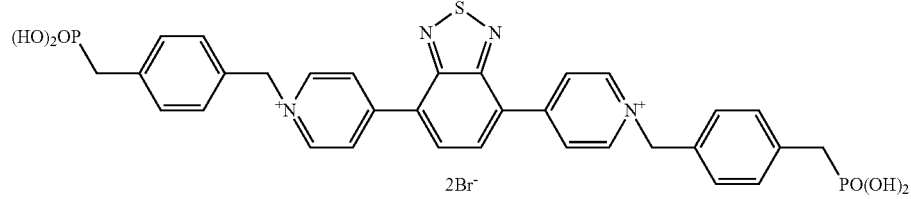
FORMULA (11)
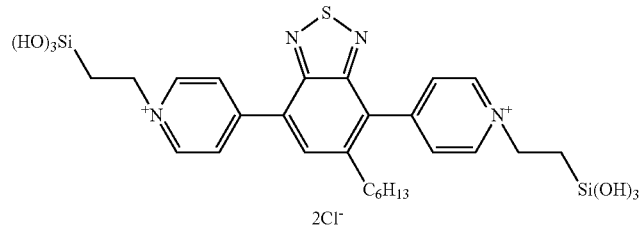
FORMULA (12)
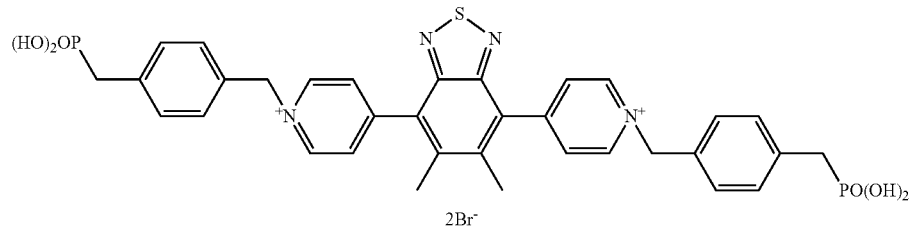
FORMULA (13)
FORMULA (14)
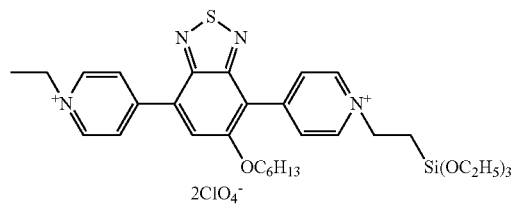
FORMULA (15)
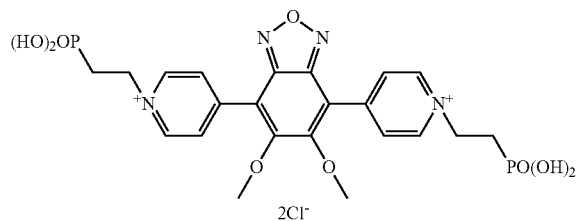
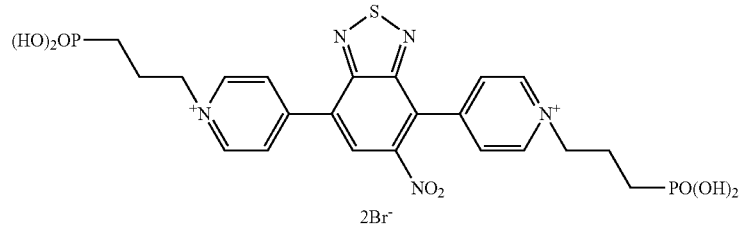
FORMULA (16)
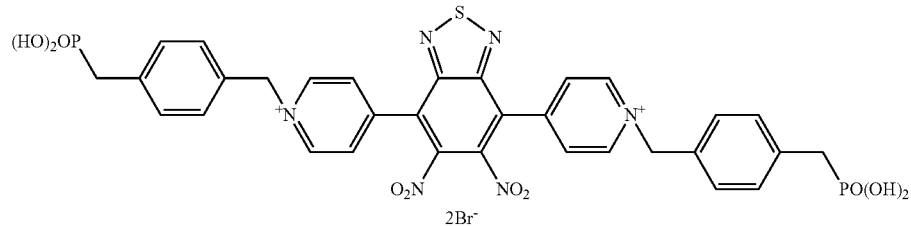
FORMULA (17)

-continued
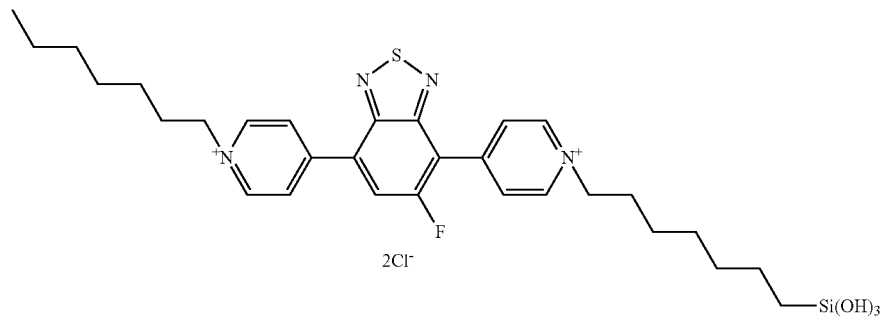
FORMULA (18)
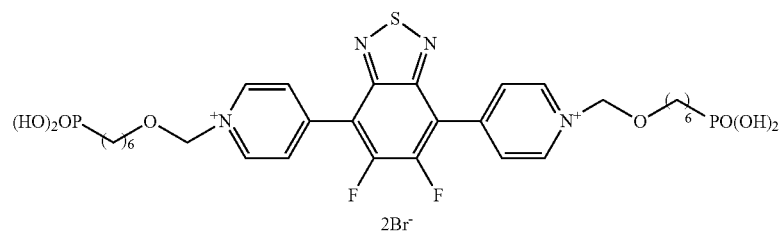
FORMULA (19)
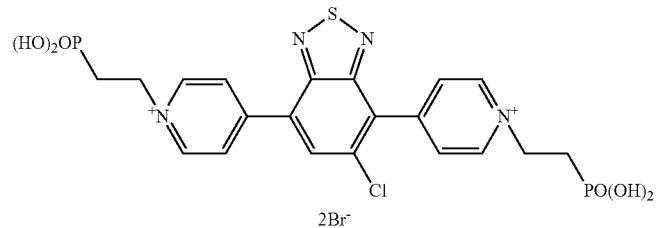
FORMULA (20)
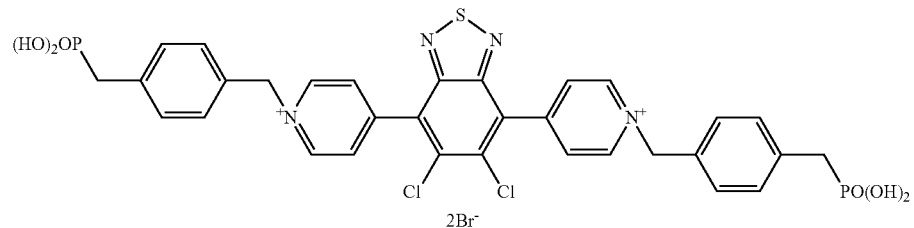
FORMULA (21)
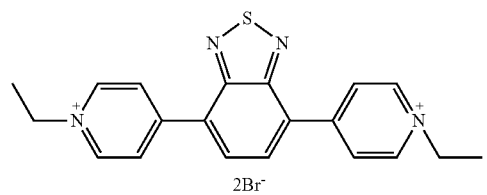
FORMULA (22)
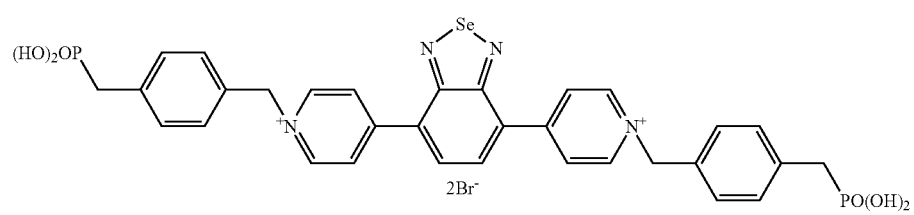
FORMULA (23)

FORMULA (24)
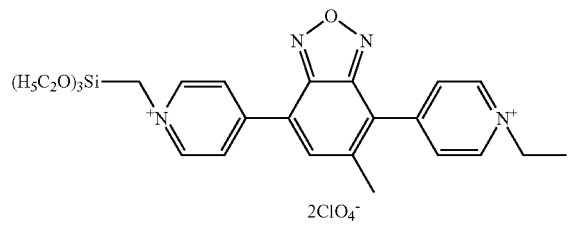
FORMULA (25)
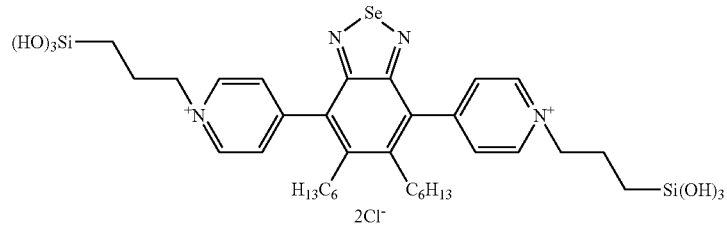
FORMULA (26)
FORMULA (27)
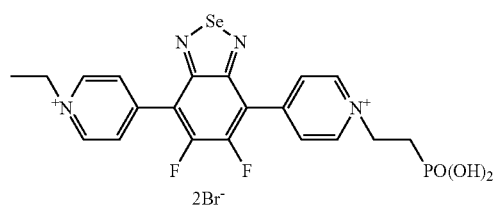 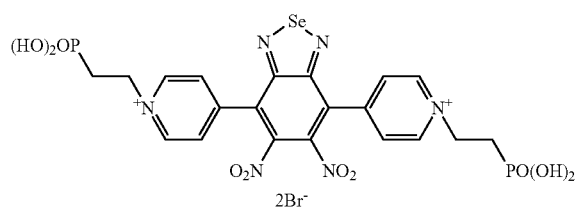
FORMULA (28)
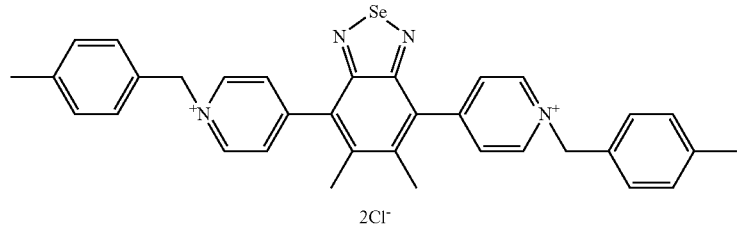
FORMULA (29)
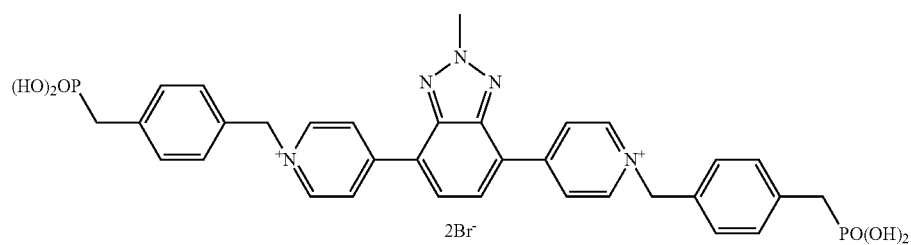

-continued
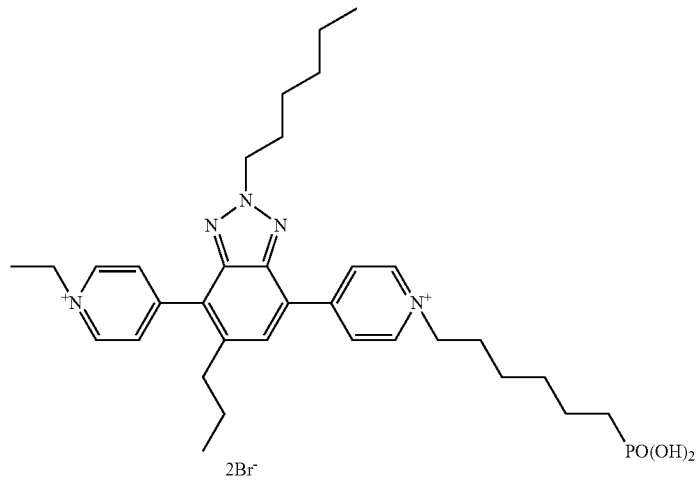
FORMULA (30)
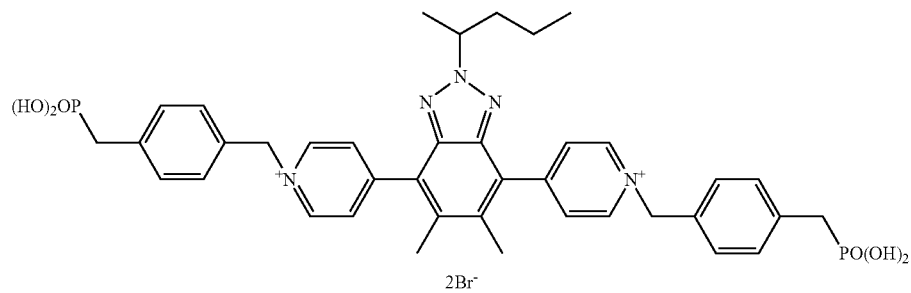
FORMULA (31)
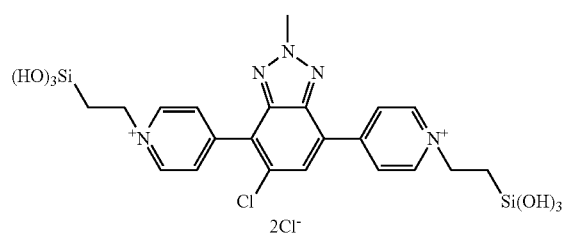
FORMULA (32)
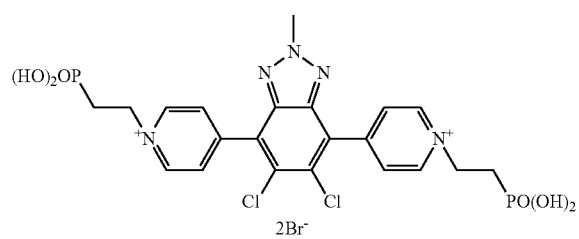
FORMULA (33)
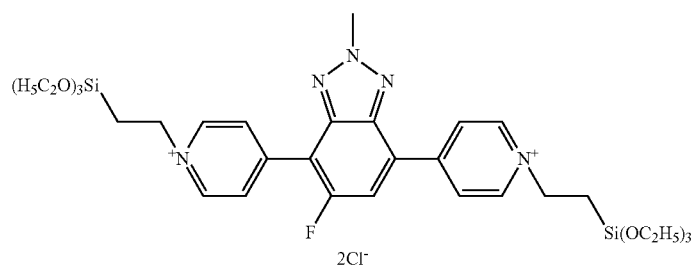
FORMULA (34)
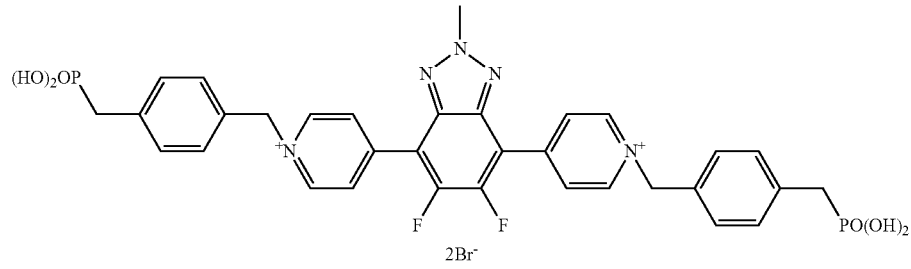
FORMULA (35)

FORMULA (36)
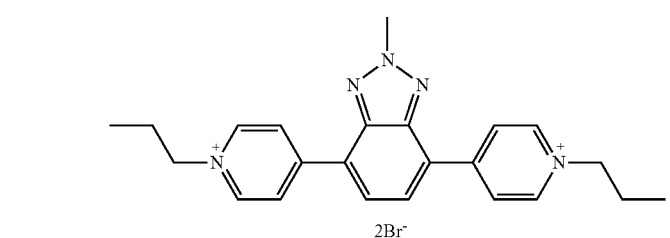
FORMULA (37)
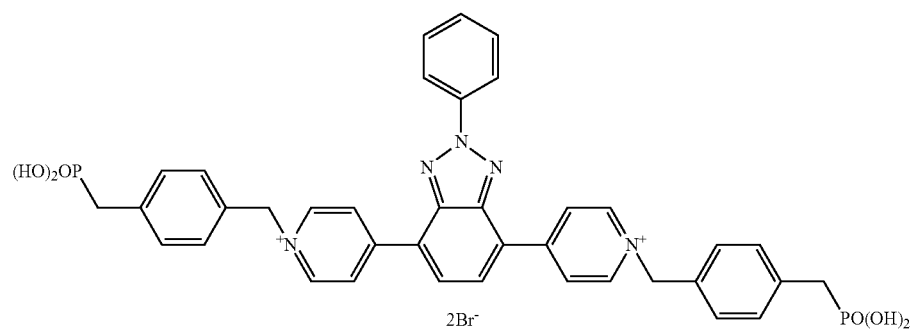
FORMULA (38)
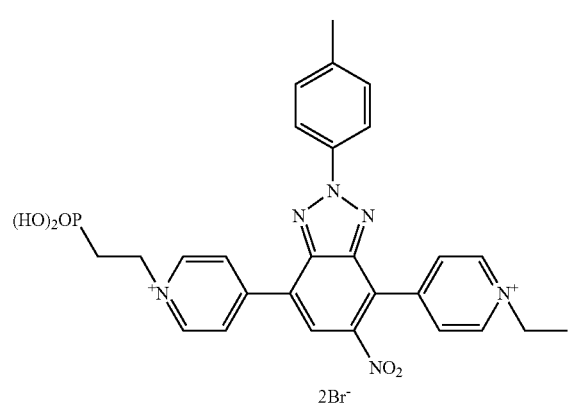
FORMULA (39)
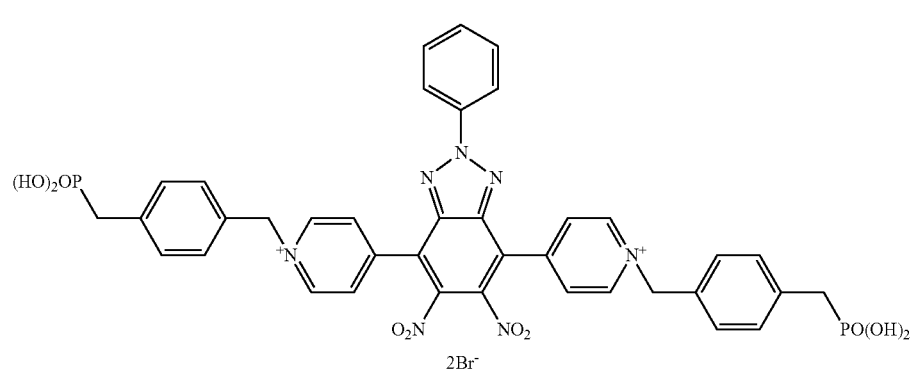

FORMULA (40)

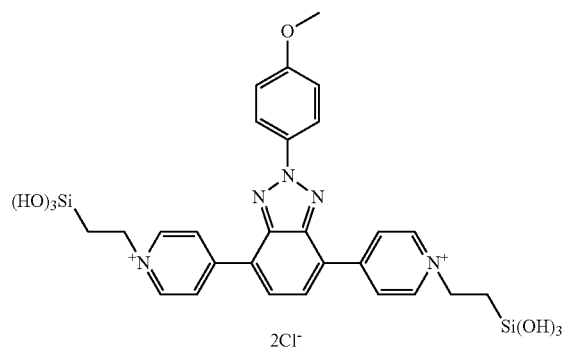

FORMULA (41)

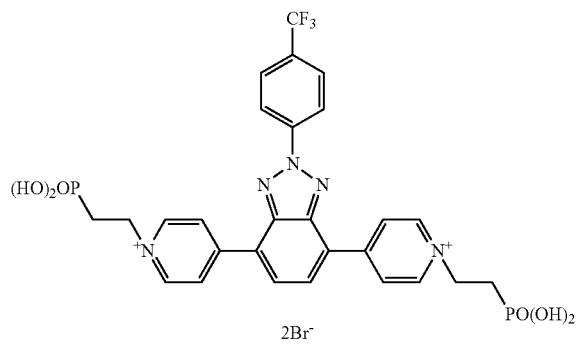

FORMULA (42)

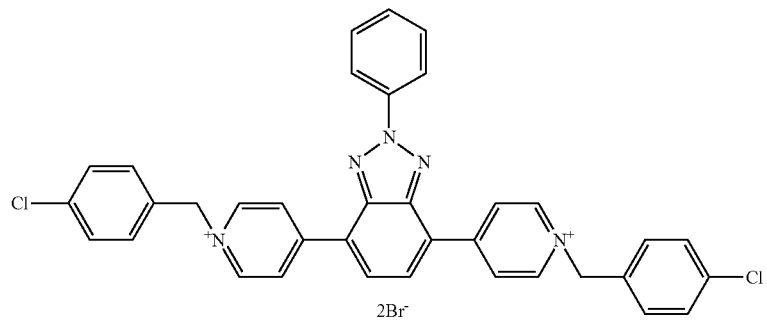

(Electrochromic Composition)

The electrochromic composition according to the present embodiment includes a conductive or semi-conductive nanostructure to which the electrochromic compound of the present embodiment represented by General Formula (1) is bound or adsorbed. The electrochromic composition according to the present embodiment may be used in an electrochromic display device to enable coloration and achieve desirable color image retaining characteristics (image memory characteristics), for example. It is noted that the conductive or semi-conductive nanostructure used in the present embodiment may be a nanoparticle, a nanoporous structure, or some other type of structure having a nanoscale roughness.

In one preferred embodiment, the electrochromic compound may include a sulfonate group, a phosphate group, or a carboxyl group as an adsorption structure so that the electrochromic compound may easily bond with the nanostructure to form a composite structure and desirable color image retaining characteristics may be achieved in the electrochromic composition. It is noted that the electrochromic compound may include more than one of the sulfonate group, the phosphate group, and the carboxyl group.

In another preferred embodiment, the electrochromic compound may bond with the nanostructure through a silanol bond so that strong bonding and stability may be achieved in the electrochromic composition. A silanol bond refers to a chemical bond for silicon atoms and oxygen atoms. It is noted that this preferred embodiment does not limit the bonding of the electrochromic compound to a particular bonding method or form so long as the electrochromic compound and the nanostructure are bonded through a silanol bond.

The conductive or semi-conductive nanostructure is preferably made of a metal oxide in order to achieve the desired transparency and conductivity. Examples of such metal oxides include those containing the following materials as a base: titanium oxide, zinc oxide, tin oxide, zirconium oxide, cerium oxide, yttrium oxide, boron oxide, magnesium oxide, strontium titanate, potassium titanate, barium titanate, calcium titanate, calcium oxide, ferrite, hafnium oxide, tungsten oxide, iron oxide, copper oxide, nickel oxide, cobalt oxide, barium oxide, strontium oxide, vanadium oxide, aluminosilicate, calcium phosphate, and aluminosilicate. It is noted that one of the above metal oxides may be used or two or more of the above metal oxides may be combined and used to fabricate the conductive or semi-conductive nanostructure. In one preferred embodiment, to enable multicolor display with a desirable coloration/decoloration response speed, one or a combination of the following materials may be used: titanium oxide, zinc oxide, tin oxide, zirconium oxide, iron oxide, magnesium oxide, indium oxide, and tungsten oxide. These materials are preferably used in view of their electric properties (e.g., conductivity) and their physical properties (e.g., optical properties). In particular, titanium oxide is preferably used to achieve a desired coloration/decoloration response speed for multicolor display.

Also, the metal oxide is preferably arranged into metal oxide particles with an average particle diameter of no more than 30 nm. It is noted that the smaller the particle size, the higher the light transmittance and the greater the surface area per unit volume (referred to as "specific surface area" hereinafter). By securing a large specific surface area, the electrochromic compound may be held more efficiently and multicolor display with a desirable coloration/decoloration display contrast ratio may be achieved. Although the specific surface area of the nanostructure is not limited, for example, the specific surface area may be arranged to be at least 100 $m^2/g$.

[Second Embodiment]

In the following, a display device according to a second embodiment of the present invention is described. The display device according to the present embodiment uses the electrochromic compound or the electrochromic composition according to the first embodiment.

Figure 1B:
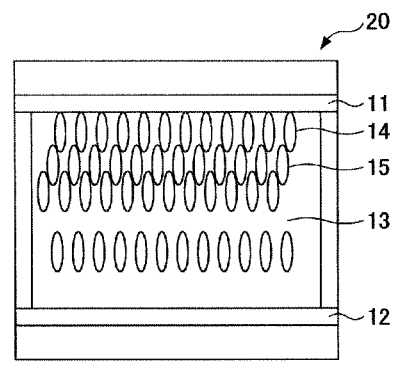

FIGS. 1A and 1B show exemplary configurations of the display device according to the present embodiment. The display devices 10 and 20 shown in FIGS. 1A and 1B include a display electrode 11, a counter electrode 12 arranged opposite the display electrode 11, an electrolyte 13 arranged between the display electrode 11 and the counter electrode 12, and a display layer 14 including an electrochromic compound 15 according to the first embodiment arranged on the surface of the display electrode 11 facing the counter electrode 12.

In the display device 10 shown in FIG. 1A, the display layer 14 uses the electrochromic compound 15 according to the first embodiment and is formed on the surface of the display electrode 11 facing the counter electrode 12. Although, the method for forming the display layer 14 is not limited to a particular method, for example, immersion, dipping, vapor deposition, spin coating, printing, or the inkjet method may be used.

Figure 2:
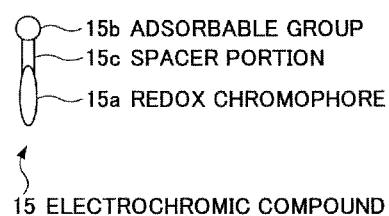
FIG. 2 shows an exemplary configuration of an electrochromic compound used in the display device shown in FIG. 1A.

FIG. 2 shows a molecular structure of the electrochromic compound 15 used in the display device 10 shown in FIG. 1A. In FIG. 2, the electrochromic compound 15 includes an adsorbable group (bonding group) 15b that is adsorbed or bound to the display electrode 11. The electrochromic compound 15 also includes a redox chromophore 15a that is attached to the adsorbable group via a spacer portion 15c. The redox chromophore 15a causes coloration/decoloration through a redox reaction.

In the display device 20 shown in FIG. 1B, the electrolyte 13 is dissolved in a solvent and the electrochromic compound 15 is also dissolved in this solvent. In this case, the electrochromic compound 15 causes coloration/decoloration through a redox reaction only at the surface of the display electrode 11 facing the counter electrode 12. That is, the display layer 14 corresponds to a portion of the solvent including the electrochromic compound 15 that is arranged on the surface of the display electrode 11 facing the counter electrode 12.

Figure 3:
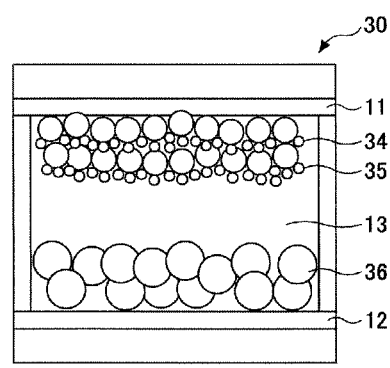
FIG. 3 shows another exemplary configuration of the display device according to the second embodiment.

FIG. 3 shows another exemplary configuration of the display device according to the present embodiment. A display device 30 shown in FIG. 3 uses an electrochromic composition 35 according to the first embodiment. The display device 30 includes the display electrode 11, the counter electrode 12 arranged opposite the display electrode 11, the electrolyte 13 arranged between the display electrode 11 and the counter electrode 12, a display layer 34 including the electrochromic composition 35 arranged on the surface of the display electrode 11 facing the counter electrode 12, and a white reflective layer 36 including white particles arranged on the surface of the counter electrode 12 facing the display electrode 11.

In the display device 30 shown in FIG. 3, the display layer 34 has the electrochromic composition 35 according to the first embodiment arranged on the surface of the display electrode 11 facing the counter electrode 12. Although, the method for forming the display layer 34 is not limited to a particular method, for example, immersion, dipping, vapor deposition, spin coating, printing, or the inkjet method may be used. The electrochromic composition 35 used in the present embodiment includes the electrochromic compound 15 that has a molecular structure as is shown in FIG. 2 including the adsorbable group 15b and a conductive or semi-conductive nanostructure that bonds with the adsorbable group (bonding group) 15b. The electrochromic composition 35 is arranged into a layer on the surface of the display electrode 11 to form the display layer 34.

In the following, exemplary materials used for the display devices 10, 20, and 30 are described.

As for the display electrode 11, a transparent conductive substrate is preferably used. Preferred examples of such a transparent conductive substrate include a glass film or a plastic film on which a transparent conductive film is formed through coating. It is noted that a plastic film substrate may preferably be used to fabricate a light, flexible display device.

Although the material for the transparent conductive film is not limited to a particular material, a transparent conductive material with adequate light transmittance and conductivity is preferably used in order to enhance the visibility of the colors produced. Examples of such a transparent conductive material include inorganic materials such as tin-doped indium oxide (referred to as "ITO" hereinafter), fluorine-doped tin oxide (referred to as "FTO" hereinafter), and antimony-doped tin oxide (referred to as "ATO" hereinafter). Particularly, an inorganic material including one of indium oxide (referred to as "In oxide" hereinafter), tin oxide (referred to as "Sn oxide" hereinafter), or zinc oxide (referred to as "Zn oxide" hereinafter) is preferably used. The In oxide, Sn oxide, and the Zn oxide are materials that may be easily formed into a film through sputtering and have the desired transparency and conductivity. Specific examples of preferred materials include InSnO, GaZnO, SnO, $In_2O_3$, and ZnO.

As for the counter electrode 12, a transparent conductive film made of ITO, FTC, or zinc oxide, a conductive metal film made of zinc or platinum, or carbon may be used, for example. The counter electrode 12 may be formed on a substrate that is preferably made of a glass plate or a plastic film.

In one embodiment, a metal plate such as a zinc plate may be used to form the counter electrode 12 in which case the counter electrode 12 may also act as a substrate.

In another embodiment, the material of the counter electrode 12 may include a material that causes a counterreaction countering the redox reaction caused by the electrochromic compound 15 or the electrochromic composition 35 of the display layer 14 or 34 so that stable coloration/decoloration may be ensured. That is, in a case where the electrochromic compound/composition produces colors through oxidation, a material that causes an reduction reaction may be used; and in a case where the electrochromic compound/composition produces colors through a reduction reaction, a material that causes oxidation may be used in the counter electrode 12 so that coloration/decoloration reactions the display layer 14 or 34 including the electrochromic compound 15 or electrochromic composition 35 may be stabilized.

As for the electrolyte 13, a solution including a supporting salt dissolved in a solvent may typically be used. Examples of the supporting salt used in the electrolyte 13 include inorganic ion salt such as alkali metal salt or alkaline-earth metal salt, quaternary ammonium salt or acids, and alkali supporting salts. Specific examples of the supporting salt include $LiClO_4$, $LiBF_4$, $LiAsF_6$, $LiPE_6$, $CF_3SO_3Li$, $CF_3COOLi$, KCl, $NaClO_3$, NaCl, $NaBF_4$, NaSCN, $KBF_4$, $Mg(ClO_4)_2$, and $Mg(BF_4)_2$.

Examples of the solvent used in the electrolyte 13 include propylene carbonate, acetonitrile, gamma-butyrolactone, ethylene carbonate, sulfolane, dioxolan, tetrahydrofuran, 2-methyltetrahydrofuran, dimethylsulfoxide, 1,2-dimethoxyethane, 1,2-ethoxymethoxyethane, polyethyleneglycol, and alcohols.

It is noted that the electrolyte 13 is not limited to a liquid electrolyte having a supporting salt dissolved in a solvent and in other examples, a gel-type electrolyte, a polymer electrolyte, or a solid electrolyte may be used. For example, a solid electrolyte such as a perfluorosulfonic acid-based polymer film may be used. The solution electrolyte has high ionic conductance while the solid electrolyte causes no degradation and is therefore suitable for producing durable devices.

When the display device of the present embodiment is used as a reflective display device as in the example illustrated in FIG. 3, the white reflective layer 36 is preferably arranged between the display electrode 11 and the counter electrode 12. In one preferred embodiment, the white reflective layer 36 may be formed by dispersing white pigment particles in resin and then applying the resulting product to the counter electrode 12. Examples of the white pigment particles include a fine particle made of commonly used metal oxides such as titanium oxide, aluminum oxide, zinc oxide, silicon oxide, cesium oxide, and yttrium oxide. In another embodiment, white pigment particles may be mixed with a polymer electrolyte so that the electrolyte 13 may also act as the white reflective layer.

The method of driving the display devices 10, 20, or 30 may be selected from any known methods capable of applying a voltage and an electric current. By using a passive driving method, an inexpensive display device may be produced. By using an active driving method, a display device with high definition and high speed may be produced. The active driving method can be performed by forming an active driving element on the substrate of the counter electrode substrate.

EXAMPLES

In the following, exemplary applications of the electrochromic compound and the electrochromic composition according to the first embodiment and the display device according to the second embodiment are described.

Example 1

Example 1 is an exemplary application of the first embodiment relating to the synthesis of the electrochromic compound represented by Formula (11).

(a) Synthesis of Intermediate Compound Represented by Formula (11-1)

First, an intermediate compound represented by Formula (11-1) shown below is synthesized.

FORMULA (11-1)

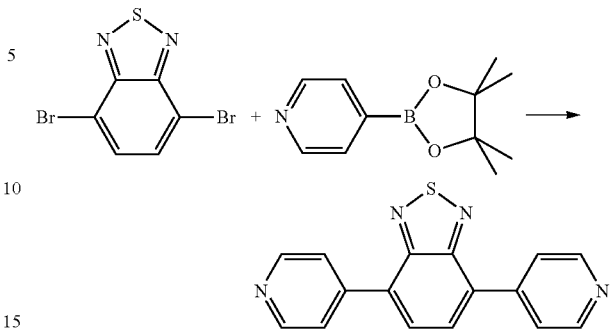

Specifically, in a 100-ml three-necked flask, 1.57 g (5.33 mmol) of 4,7-dibromo-2,1,3-benzothiadiazole, 4.92 g (24.0 mmol) of 4-(4,4,5,5-tetramethyl-1,3,2-dioxaborolan-2-yl)pyridine, 0.616 g (0.530 mmol) of tetrakis(triphenylphosphine)palladium, and 0.166 g (0.411 mmol) of Aliquat 336 (manufactured by Aldrich) as the phase-transfer catalyst are added and argon gas substitution is performed. Then, 30 ml of 1,4-dioxane that has been degassed with argon gas and 27 ml of 1M-potassium carbonate aqueous solution that has been degassed with argon gas are added in this order and the mixture is refluxed at 105° C. for 16 hours. After the reaction mixture is cooled down to room temperature, chloroform and brine are added. Then, after transferring the mixture to a separating funnel and washing the organic layer with brine, magnesium sulfate as a dehydrating agent is added to the organic layer and the mixture is stirred for 1 hour at room temperature to induce dehydration. Then, 2 g of palladium scavenger silica gel (manufactured by Aldrich) is added and the mixture is stirred for 1 hour at room temperature to remove residual palladium within the organic layer. After filtering out the dehydrating agent and the silica gel, the solvent is removed through vacuum distillation. The resulting crude product is then purified through silica gel column chromatography (toluene/acetone=1/2) to obtain the target product (yield amount: 1.05 g, yield rate: 68%).

(b) Synthesis of Electrochromic Compound Represented by Formula (11)

Using the intermediate compound represented by Formula (11-1), the electrochromic compound represented by Formula (11) is synthesized as is shown below.

FORMULA (11)

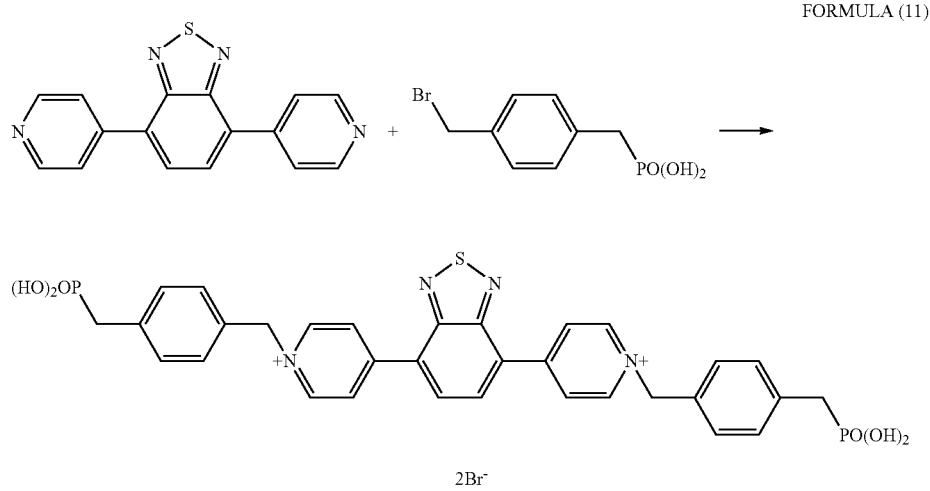

Specifically, in a 25-ml three-necked flask, 0.116 g (0.40 mmol) of 4,7-bis(4-pyridyl)-2,1,3-benzothiadiazole, 0.371 g (1.40 mmol) of 4-bromomethylbenzylphosphonic acid, 2.5 ml of dimethylformamide are added and the mixture is reacted for 3 hours at 90° C. After the mixture cools down to room temperature, it is discharged in 2-propanol, and the resulting solid is dispersed in the 2-propanol and collected thereafter. Then, the resulting product is dried in vacuum for 2 days at 100° C. to obtain the target product (yield amount: 0.30 g, yield rate: 91%).

Example 2

Example 2 is an exemplary application of the first embodiment relating to the synthesis of the electrochromic compound represented by Formula (13).

(a) Synthesis of Intermediate Compound Represented by Formula (13)

First, an intermediate compound represented by Formula (13-1) shown below is synthesized.

FORMULA (13-1)

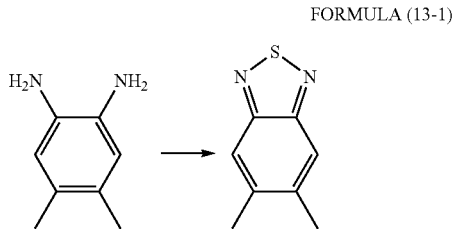

Specifically, in an argon-gas-substituted 200-ml four-necked flask, 2.00 g (14.7 mmol) of 4,5-diamino-o-xylene, 50 ml of dichloromethane, and 8.35 ml of triethylamine are added, after which 2.18 ml (30.0 mmol) of thionyl chloride are slowly added drop by drop to the mixture. Then, the solution is refluxed for 5 hours and then dried by removing the solvent through vacuum distillation after which dichloromethane and pure water are added to the mixture. Then, the mixture is transferred to a separating funnel, the organic layer is washed, and magnesium sulfate is added, after which the mixture is stirred for 1 hour at room temperature to induce dehydration. Then, after filtering out the dehydrating agent, the solvent is removed through vacuum distillation. The resulting crude product is purified through silica gel column chromatography (hexane/acetic ether=4/1) to obtain the target product (yield amount: 1.50 g, yield rate: 63%).

(b) Synthesis of Intermediate Compound Represented by Formula (13-2)

Then, an intermediate compound represented by Formula (13-2) shown below is synthesized.

FORMULA (13-2)

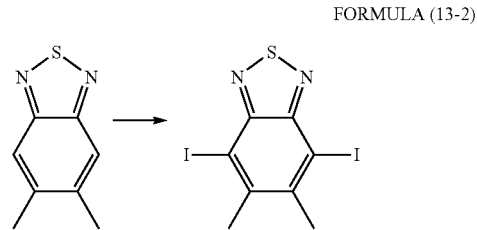

Specifically, in a 200-ml four-necked flask, 1.50 g (9.10 mmol) of 5,6-dimethyl-2,1,3-benzothiadiazole, 2.54 g (9.98 mmol) of iodine, 0.90 g (4.53 mmol) of sodium iodate, 1.9 ml of sulfuric acid, 31 ml of acetic acid and 0.23 ml of pure water are added and the mixture is refluxed for 16 hours at 120° C. After the mixture cools down to room temperature, a sodium sulfite aqueous solution is added to the reaction mixture until the coloring by the iodine disappears. Then, the mixture is transferred to a separating funnel and extraction is performed three times using dichloromethane after which the organic layer is washed with brine. Then, magnesium sulfate is added and the mixture is stirred for 1 hour at room temperature to induce dehydration after which the dehydrating agent is filtered out and the solvent is removed through vacuum distillation. The resulting crude product is purified through silica gel column chromatography (hexane/acetic ether=4/1) to obtain the target product (yield amount: 3.30 g, yield rate: 87%).

(C) Synthesis of Intermediate Compound Represented by Formula (13-3)

Then, an intermediate compound represented by Formula (13-3) shown below is synthesized.

FORMULA (13-3)

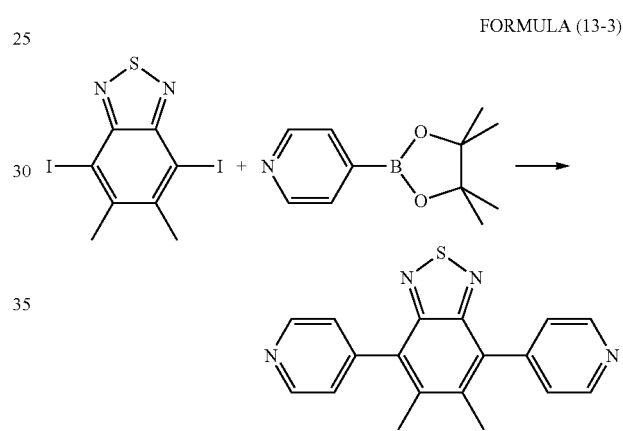

Specifically, in a 100-ml three-necked flask, 1.00 g (2.40 mmol) of 4,7-diiodo-5,6-dimethyl-2,1,3-benzothiadiazole, 2.22 g (10.8 mmol) of 4-(4,4,5,5-tetramethyl-1,3,2-dioxaborolan-2-yl)pyridine, 0.278 g (0.240 mmol) of tetrakis(triphenylphosphine)palladium, and 0.110 g (0.272 mmol) of Aliquat 336 (manufactured by Aldrich) as the phase-transfer catalyst are added and argon gas substitution is performed. Then, 23 ml of 1,4-dioxane that has been degassed with argon gas and 18 ml of 1M-potassium carbonate aqueous solution that has been degassed with argon gas are added in this order and the reaction mixture is refluxed at 105° C. for 45 hours. After the reaction mixture returns to room temperature, chloroform and brine are added. Then, after transferring the mixture to a separating funnel and washing the organic layer with brine, magnesium sulfate as a dehydrating agent is added to the organic layer and the mixture is stirred for 1 hour at room temperature to induce dehydration. Then, 1 g of palladium scavenger silica gel (manufactured by Aldrich) is added and the mixture is stirred for 1 hour at room temperature to remove residual palladium within the organic layer. After filtering out the dehydrating agent and the silica gel, the solvent is removed through vacuum distillation. The resulting crude product is then purified through silica gel column chromatography (toluene/acetone=1/1) to obtain the target product (yield amount: 0.37 q, yield rate: 48%).

(d) Synthesis of Electrochromic Compound Represented by Formula (13)

Then, using the intermediate compound represented by (13-3), the electrochromic compound represented by Formula (13) is synthesized as is shown below.

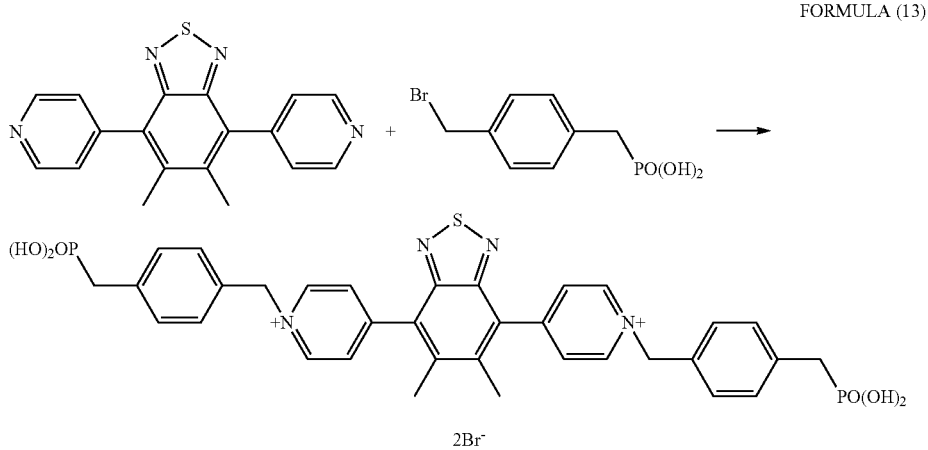

FORMULA (13)

Specifically, in a 25-ml three-necked flask, 0.127 g (0.40 mmol) of 4,7-bis(4-pyridyl)-5,6-dimethyl-2,1,3-benzothiadiazole, 0.371 g (1.40 mmol) of 4-bromomethylbenzylphosphonic acid, and 2.3 ml of dimethylformamide are added and the mixture is reacted for 3 hours at 90° C. After the mixture cools down to room temperature, it is discharged in 2-propanol, and the resulting solid is dispersed in the 2-propanol and collected thereafter. Then, the resulting product is dried in vacuum for 2 days at 100° C. to obtain the target product (yield amount: 0.34 g, yield rate: 93%).

Example 3

Example 3 is an exemplary application of the first embodiment relating to the synthesis of the electrochromic compound represented by Formula (3).

(a) Synthesis of Intermediate Compound Represented by Formula (3-1)

First, an intermediate compound represented by Formula (3-1) shown below is synthesized.

FORMULA (3-1)

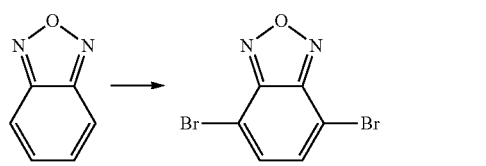

Specifically, in a 100-ml three-necked flask, 2.30 g (19.2 mmol) of 2,1,3-benzooxadiazole and 0.21 g (3.83 mmol) of iron powder are added and heated at 90° C. Then, 3 ml of bromine is slowly added drop by drop to the mixture over a period of 1.5 hours and the mixture is then reacted for 3 hours. After the reaction mixture cools down to room temperature, it is poured into 100 ml of pure water and precipitated solids are collected. Then, the collected solids are mixed with 100 ml of saturated aqueous sodium bicarbonate solution and stirred for 1 hour after which the resulting product is collected, dried, and re-crystallized with ethanol to obtain the target product (yield amount: 3.06 g, yield rate: 67%).

(b) Synthesis of Intermediate Compound Represented by Formula (3-2)

Then, an intermediate compound represented by Formula (3-2) shown below is synthesized.

FORMULA (3-2)

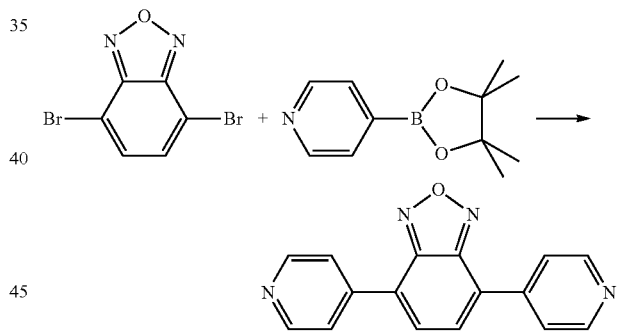

Specifically, in a 100-ml three-necked flask, 1.50 g (5.40 mmol) of 4,7-dibromo-2,1,3-benzoxadiazole, 4.92 g (24.0 mmol) of 4-(4,4,5,5-tetramethyl-1,3,2-dioxaborolan-2-yl)pyridine, 0.616 g (0.530 mmol) of tetrakis(triphenylphosphine)palladium, and 0.166 g (0.411 mmol) of Aliquat 336 (manufactured by Aldrich) as the phase-transfer catalyst are added and argon gas substitution is performed. Then, 30 ml of 1,4-dioxane that has been degassed with argon gas and 27 ml of 1M-potassium carbonate aqueous solution that has been degassed with argon gas are added in this order and the reaction mixture is refluxed at 105° C. for 30 hours. After the reaction mixture cools down to room temperature, chloroform and brine are added. Then, after transferring the mixture to a separating funnel and washing the organic layer with brine, magnesium sulfate as a dehydrating agent is added to the organic layer and the mixture is stirred for 1 hour at room temperature to induce dehydration. Then, 2 g of palladium scavenger silica gel (manufactured by Aldrich) is added and the mixture is stirred for 1 hour at room temperature to remove residual palladium within the organic layer. After filtering out the dehydrating agent and the silica gel, the solvent is removed through vacuum distillation. The resulting crude product is then purified through silica gel column chromatography (toluene/acetone=1/1) to obtain the target product (yield amount: 0.75 g, yield rate: 51%).

(c) Synthesis of Electrochromic Compound Represented by Formula (3)

Then, using the intermediate compound represented by Formula (3-2), the electrochromic compound represented by Formula (3) is synthesized as shown below,

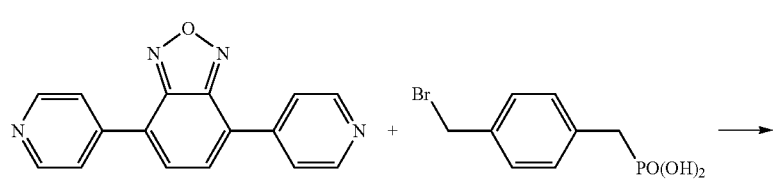

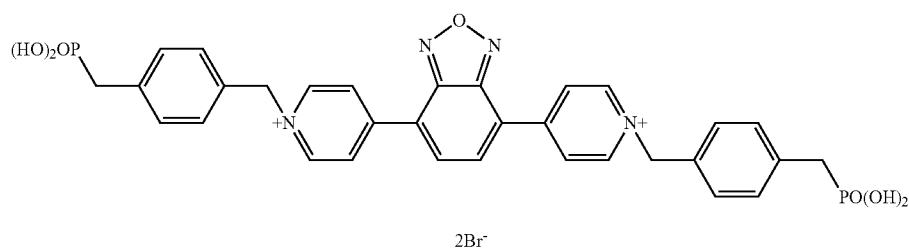

2Br⁻

Specifically, in a 25-ml three-necked flask, 0.137 g (0.50 mmol) of 4,7-bis(4-pyridyl)-2,1,3-benzoxadiazole, 0.464 g (1.75 mmol) of 4-bromomethylbenzylphosphonic acid, and 2.6 ml of dimethylformamide are added and the mixture is reacted for 2.5 hours at 90° C. After the mixture cools down to room temperature, it is discharged in 2-propanol, and the resulting solid is dispersed in the 2-propanol and collected thereafter. Then, the resulting product is dried in vacuum for 2 days at 100° C. to obtain the target product (yield amount: 0.38 g, yield rate: 95%).

Example 4

Example 4 is an exemplary application of the first embodiment relating to the synthesis of the electrochromic compound represented by Formula (23).

(a) Synthesis of Intermediate Compound Represented by Formula (23-1)

First, an intermediate compound represented by Formula (23-1) shown below is synthesized.

FORMULA (23-1)

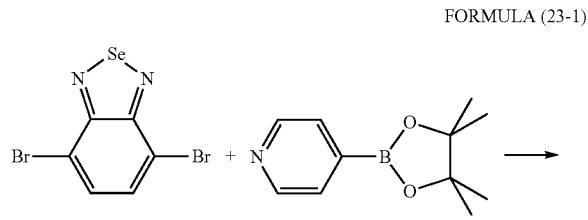

-continued

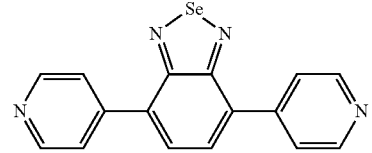

Specifically, in a 100-ml three-necked flask, 1.21 g (3.55 mmol) of 4,7-dibromo-2,1,3-benzoselenadiazole, 3.35 g (16.3 mmol) of 4-(4,4,5,5-tetramethyl-1,3,2-dioxaborolan-2-yl)pyridine, 0.41 g (0.36 mmol) of tetrakis(triphenylphosphine)palladium, and 0.130 g (1.90 mmol) of Aliquat 336 (manufactured by Aldrich) as the phase-transfer catalyst are added and argon gas substitution is performed. Then, 20 ml of 1,4-dioxane that has been degassed with argon gas and 20 ml of 1M-potassium carbonate aqueous solution that has been degassed with argon gas are added in this order and the reaction mixture is refluxed at 105° C. for 24 hours. After the reaction mixture cools down to room temperature, chloroform and brine are added. Then, after transferring the mixture to a separating funnel and washing the organic layer with brine, magnesium sulfate as a dehydrating agent is added to the organic layer and the mixture is stirred for 1 hour at room temperature to induce dehydration. Then, 1 g of palladium scavenger silica gel (manufactured by Aldrich) is added and the mixture is stirred for 1 hour at room temperature to remove residual palladium within the organic layer. After filtering out the dehydrating agent and the silica gel, the solvent is removed through vacuum distillation. The resulting crude product is then purified through silica gel column chromatography (toluene/acetone=1/2) to obtain the target product (yield amount: 0.51 g, yield rate: 43%).

(b) Synthesis of Electrochromic Compound Represented by Formula (23)

Then, using the intermediate compound represented by Formula (23-1), the electrochromic compound represented by Formula (23) is synthesized as is shown below.

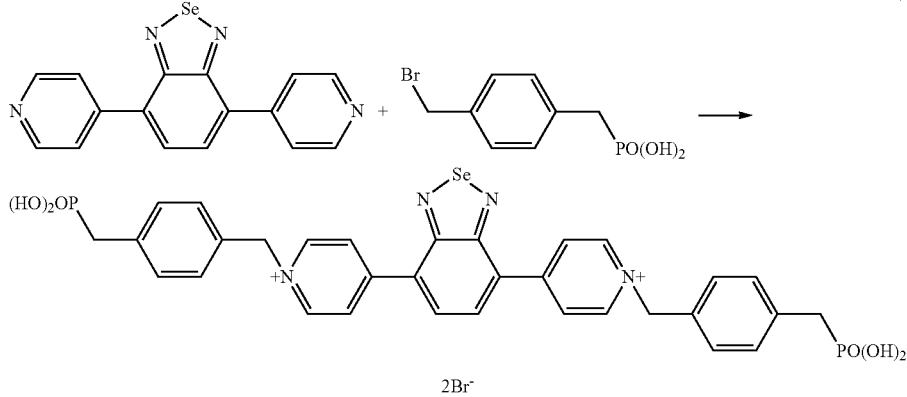

FORMULA (23)

Specifically, in a 25-ml three-necked flask, 0.134 g (0.40 mmol) of 4,7-bis(4-pyridyl)-2,1,3-benzoselenadiazole, 0.371 g (1.40 mmol) of 4-bromomethylbenzylphosphonic acid, and 2.4 ml of dimethylformamide are added and the mixture is reacted for 3 hours at 90° C. After the reaction mixture cools down to room temperature, it is discharged in 2-propanol, and the resulting solid is dispersed in the 2-propanol and collected thereafter. Then, the resulting product is dried in vacuum for 2 days at 100° C. to obtain the target product (yield amount: 0.30 g, yield rate: 87%).

Example 5

Example 5 is an exemplary application of the first embodiment relating to the synthesis of the electrochromic compound represented by Formula (29).

(a) Synthesis of Intermediate Compound Represented by Formula (29-1)

First, an intermediate compound represented by Formula (29-1) shown below is synthesized.

FORMULA (29-1)

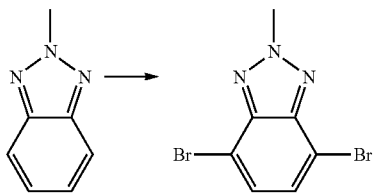

Specifically, in a 100-ml three-necked flask, 1.50 g (11.3 mmol) of 2-methyl-2H-benzotriazole and 0.06 g (1.12 mmol) of iron powder are added and heated to 90° C. Then, 3.6 ml (147 mmol) of bromine is slowly added to the mixture using a dropping funnel and the mixture is then reacted for 3 hours. After the mixture cools down to room temperature, 100 ml of pure water and 100 ml of saturated aqueous sodium bicarbonate solution are added and the mixture is stirred and washed for 1 hour and filtered. The resulting solids are then re-crystallized with ethanol so that a mixture of 4,7-dibromo-2-methyl-2H-benzotriazole, which is the target product, and 4,5,7-tribromo-2-methyl-2H-benzotriazole is obtained. Then, the target product is separated and purified from the above mixture using the Recycling Preparative Gel Permeation Chromatography (GPC) (manufactured by Japan Analytical Industry Co., Ltd.) which uses tetrahydrofuran as the eluent (yield amount: 0.95 g, yield rate: 30%).

(b) Synthesis of Intermediate Compound Represented by Formula (29-2)

Then, an intermediate compound represented by Formula (29-2) shown below is synthesized.

FORMULA (29-2)

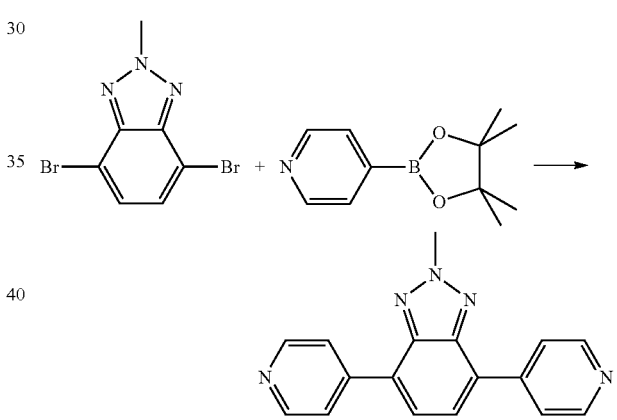

Specifically, in a 100-ml three-necked flask, 0.60 g (2.06 mmol) of 4,7-dibromo-2-methyl-2H-benzotriazole, 1.86 g (9.07 mmol) of 4-(4,4,5,5-tetramethyl-1,3,2-dioxaborolan-2-yl)pyridine, 0.240 g (0.206 mmol) of tetrakis(triphenylphosphine)palladium, and 0.100 g (0.250 mmol) of Aliquat 336 (manufactured by Aldrich) as the phase-transfer catalyst are added and argon gas substitution is performed. Then, 19 ml of 1,4-dioxane that has been degassed with argon gas and 15 ml of 1M-potassium carbonate aqueous solution that has been degassed with argon gas are added in this order and the reaction mixture is refluxed at 105° C. for 5 hours. After the reaction mixture cools down to room temperature, chloroform and brine are added. Then, after transferring the mixture to a separating funnel and washing the organic layer with brine, magnesium sulfate as a dehydrating agent is added to the organic layer and the mixture is stirred for 1 hour at room temperature to induce dehydration. Then, 1 g of palladium scavenger silica gel (manufactured by Aldrich) is added and the mixture is stirred for 1 hour at room temperature to remove residual palladium within the organic layer. After filtering out the dehydrating agent and the silica gel, the solvent is removed through vacuum distillation. The resulting crude product is then purified through silica gel column chromatography (toluene/acetone=1/1) to obtain the target product (yield amount: 0.43 g, yield rate: 73%).

(c) Synthesis of Electrochromic Compound Represented by Formula (29)

Then, using the intermediate compound represented by Formula (29-2), the electrochromic compound represented by Formula (29) is synthesized as is shown below.

ture. Then dichloromethane is added to perform extraction, and 1N hydrochloric acid is used to wash the mixture. After washing the organic layer with water, saturated aqueous sodium bicarbonate solution, and brine solution in this order, sodium sulfate is added to dry the organic layer. Then, the solvent is removed through vacuum distillation and the resulting mixture is re-crystallized with ethanol to obtain the target product (yield amount: 5.43 g, yield rate: 78%).

FORMULA (29)

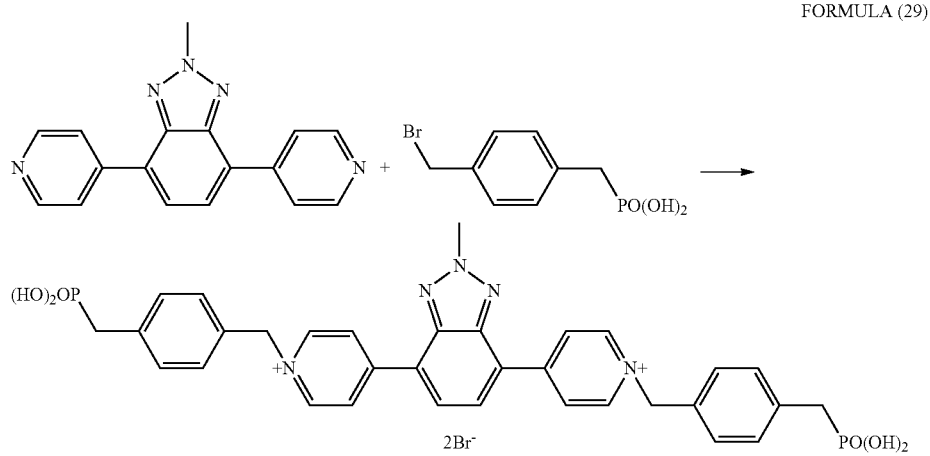

Specifically, in a 25-ml three-necked flask, 0.114 g (0.40 mmol) of 4,7-bis(4-pyridyl)-2-methyl-2H-benzotriazole, 0.371 g (1.40 mmol) of 4-bromomethylbenzylphosphonic acid, 3.4 ml of dimethylformamide are added and the mixture is reacted for 1.5 hours at 90° C. After the reaction mixture cools down to room temperature, it is discharged in 2-propanol, and the resulting solid is dispersed in the 2-propanol and collected thereafter. Then, the resulting product is dried in vacuum for 2 days at 100° C. to obtain the target product (yield amount: 0.31 g, yield rate: 95%).

Example 6

Example 6 is an exemplary application of the first embodiment relating to the synthesis of the electrochromic compound represented by Formula (37).

(a) Synthesis of Intermediate Compound Represented by Formula (37-1)

First, an intermediate compound represented by Formula (37-1) shown below is synthesized.

FORMULA (37-1)

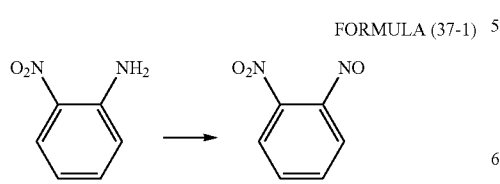

Specifically, in a 1000-ml three-necked flask, 350 ml of dichloromethane and 125 ml of water are mixed, 12.5 g (45.2 mmol) of 2-nitroaniline and 46.5 g (75 mmol) of oxone are added, and the mixture is stirred for 4 days at room tempera- (b) Synthesis of Intermediate Compound Represented by Formula (37-2)

Then, an intermediate compound represented by Formula (37-2) shown below is synthesized.

FORMULA (37-2)

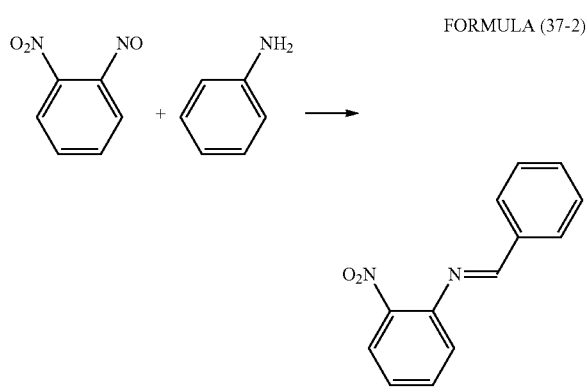

Specifically, in a 500-ml three-necked flask, 2.8 g (4.6 mmol) of 1-nitro-2-nitrosobenzene, 1.7 g (4.6 mmol) of aniline, and 200 ml of acetic acid are added and stirred for 48 hours at room temperature. The mixture is then placed in ice water, and the precipitated crude product is filtered and collected. The crude product is purified using silica gel column chromatography (dichloromethane) to obtain the target product (yield amount: 3.23 g, yield rate: 74%).

(c) Synthesis of Intermediate Compound Represented by Formula (37-3)

Then, an intermediate compound represented by Formula (37-3) shown below is synthesized.

(e) Synthesis of Intermediate Compound Represented by Formula (37-5)

Then, an intermediate product represented by Formula (37-5) shown below is synthesized.

FORMULA (37-3)

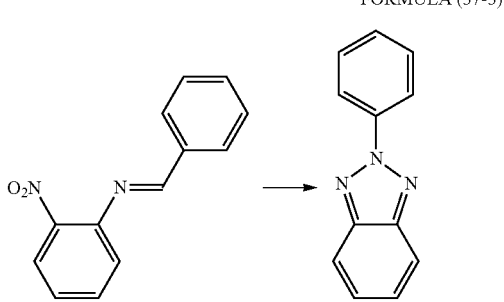

Specifically, in a 200-ml three-necked flask, 2.4 g (2.6 mmol) of 1-(2-nitrophenyl)-2-phenyldiazene, 40 ml of ethanol, and 25 ml of 4N sodium hydroxide aqueous solution are added and stirred at 80° C. Then, 3.9 g (36 mmol) of formamidinesulfinic acid is slowly added to this mixture and the resulting mixture is stirred for 90 minutes. Then, this mixture is poured into ice water and the precipitated crude product is filtered and collected. The crude product is then re-crystallized with ethanol to obtain the target product (yield amount: 1.61 g, yield rate: 78%).

(d) Synthesis of Intermediate Compound Represented by Formula (37-4)

Then, an intermediate compound represented by Formula (37-4) shown below is synthesized.

FORMULA (37-4)

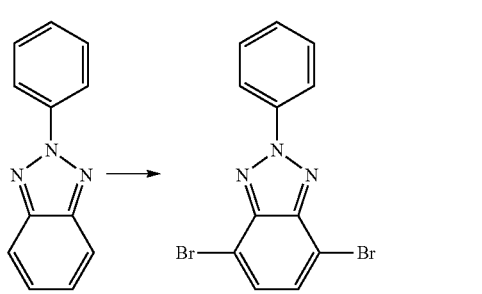

Specifically, in a 100-ml three-necked flask, 1.2 g (6.2 mmol) of 2-phenyl-2H-benzotriazole and 30 ml of hydrogen bromide (48%) are added and heated to 120° C. Then, 7.2 ml (140 mmol) of bromine is slowly added drop by drop to this mixture over a period of 5 hours and the resulting mixture is heated for 2 hours. The mixture is then poured into ice water and the precipitated crude product is washed with sodium thiosulfate water, water, and methanol in this order. The resulting crude product is then re-crystallized with ethanol to obtain the target product (yield amount: 1.11 g, yield rate: 55%).

FORMULA (37-5)

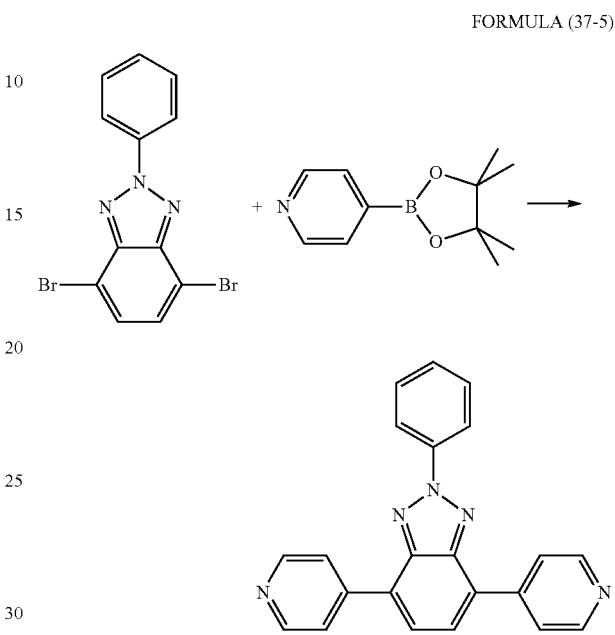

Specifically, in a 100-ml three-necked flask, 0.70 g (2.0 mmol) of 4,7-dibromo-2-phenyl-2H-benzotriazole, 1.86 g (9.1 mmol) of 4-(4,4,5,5-tetramethyl-1,3,2-dioxaborolan-2-yl)pyridine, 0.24 g (0.21 mmol) of tetrakis(triphenylphosphine)palladium, and 0.10 g (0.25 mmol) of Aliquat 336 (manufactured by Aldrich) as the phase-transfer catalyst are added and argon gas substitution is performed. Then, 19 ml of 1,4-dioxane that has been degassed with argon gas and 15 ml of 1M-potassium carbonate aqueous solution that has been degassed with argon gas are added in this order and the mixture is refluxed at 105° C. for 13 hours. After the reaction mixture is cooled down to room temperature, chloroform and brine are added. Then, after transferring the mixture to a separating funnel and washing the organic layer with brine, magnesium sulfate as a dehydrating agent is added to the organic layer and the mixture is stirred for 1 hour at room temperature to induce dehydration. Then, 1 g of palladium scavenger silica gel (manufactured by Aldrich) is added and the mixture is stirred for 1 hour at room temperature to remove residual palladium within the organic layer. After filtering out the dehydrating agent and the silica gel, the solvent is removed through vacuum distillation. The resulting crude product is then purified through silica gel column chromatography (toluene/acetone=1/1) to obtain the target product (yield amount: 0.34 g, yield rate: 48%).

(f) Synthesis of Electrochromic Compound Represented by Formula (37)

Using the intermediate compound represented by Formula (37-5), the electrochromic compound represented by Formula (37) is synthesized as is shown below.

FORMULA (37)

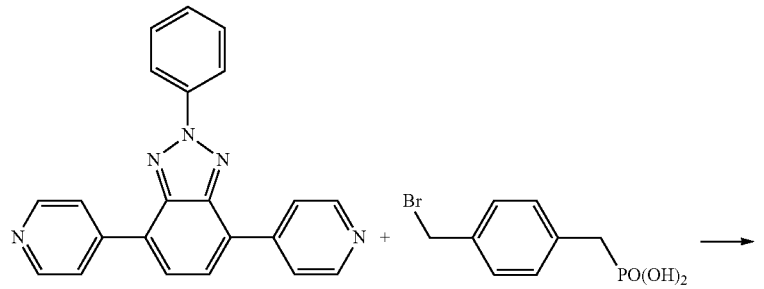

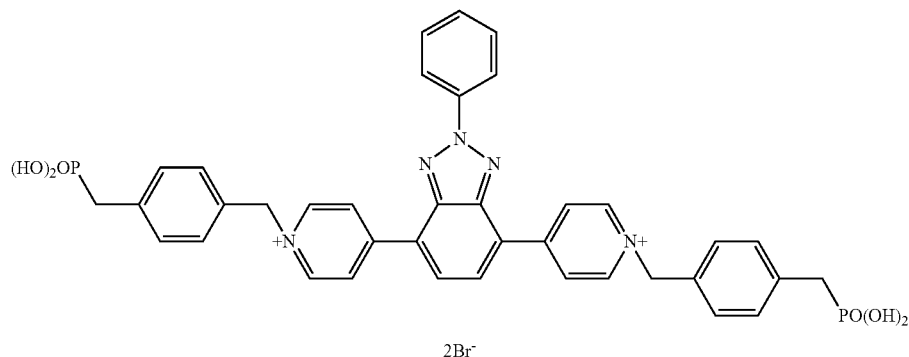

Specifically, in a 25-ml three-necked flask, 0.139 g (0.40 mmol) of 4,7-bis(4-pyridyl)-2-phenyl-2H-benzotriazole, 0.358 g (1.35 mmol) of 4-bromomethylbenzylphosphonic acid, and 3 ml of dimethylformamide are added, and the mixture is reacted for 2.5 hours at 90° C. After the reaction mixture cools down to room temperature, it is discharged in 2-propanol, and the resulting solid is dispersed in the 2-propanol and collected thereafter. Then, the resulting product is dried in vacuum for 2 days at 100° C. to obtain the target product (yield amount: 0.35 g, yield rate: 99%).

Comparative Example 1

Comparative Example 1 relates to the synthesis of the electrochromic compound described in Patent Document 11 that displays the color cyan at coloration. The electrochromic compound is represented by Formula (43) shown below.

(a) Display Electrode and Electrochromic Display Layer Fabrication

First, a 30×30 mm glass substrate is prepared, and an ITO film with a film thickness of approximately 100 nm is formed on a 16×23 mm region on the surface of the glass substrate through sputtering to form the display electrode 11. Upon measuring the sheet resistance between the edges of the display electrode 11, a measurement of approximately 200Ω was obtained.

Then, a titanium oxide nanoparticle dispersion liquid (SP210 manufactured by Showa Titanium Co., Ltd.) is applied on the glass substrate with the display electrode 11 through spin coating and an annealing process is performed at 120° C. for 15 minutes to form a titanium oxide particle film. Then, a 2,2,3,3-tetrafluoropropanol solution at an amount equal to 1 wt % of the compound represented by Formula (11) is applied through spin coating and an annealing process is

FORMULA (43)

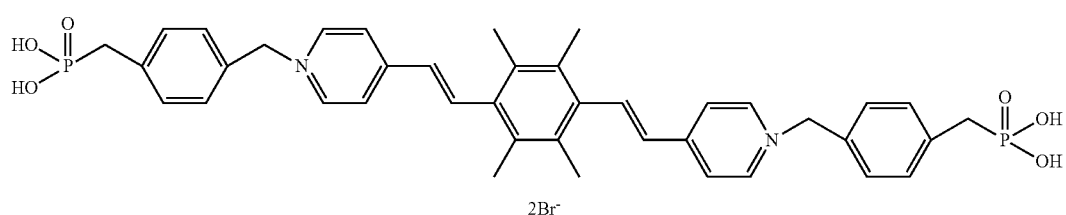

Example 7

Example 7 relates to an exemplary method of manufacturing the electrochromic display device according to the second embodiment.

performed at 120° C. for 10 minutes to form the display layer 14 having electrochromic compounds adsorbed to the surface of the titanium oxide particle film.

(b) Counter Electrode Fabrication

Meanwhile, another 30×30 mm glass substrate is prepared, and an ITO film as a transparent conductive film with a film thickness of approximately 150 nm is formed on the entire surface of this glass substrate through sputtering. Further, a solution prepared by adding 25 wt % of 2-ethoxyethyl acetate to thermosetting conductive carbon ink (CH10 manufactured by Jujo Chemical Co., Ltd) is applied on the surface of the glass substrate having the transparent conductive film formed thereon through spin coating and an annealing process is performed at 120° C. for 15 minutes to form the counter electrode 12.

(c) Electrochromic Display Device Fabrication

The substrate with the display electrode 11 and the substrate with the counter electrode 12 are bound together via a spacer having a thickness of 75 µm to form a cell. Then, 35 wt % of titanium oxide particles having a particle diameter of 300 nm is dispersed in a solution prepared by adding 20 wt % of tetrabutylammonium perchlorate to dimethyl sulfoxide to create an electrolyte solution. The electrolyte solution is then enclosed within the cell to create the electrochromic display device according to the second embodiment.

Comparative Example 2

Comparative Example 2 relates to an electrochromic display device manufactured using the electrochromic compound represented by Formula (43) synthesized in Comparative Example 1, the display device being manufactured in a manner similar to steps (a)-(c) for creating a display electrode, an electrochromic display layer, and an electrochromic display device of Example 7.

Example 8

In Example 8, a coloration/decoloration test was conducted on the electrochromic display device manufactured in Example 7.

First, a coloration/decoloration comparative evaluation was performed on the electrochromic display device manufactured in Example 7. The coloration/decoloration evaluation was performed by irradiating scattered light using a spectrophotometer (LCD-5000 manufactured by Otsuka Electronics Co., Ltd.).

Upon connecting the display electrode 11 of the display device to a negative electrode, connecting the counter electrode 12 to a positive electrode, and applying a voltage of 3.0 V for 1 second, the display device produced the color cyan in a desirable manner.

Figure 4:
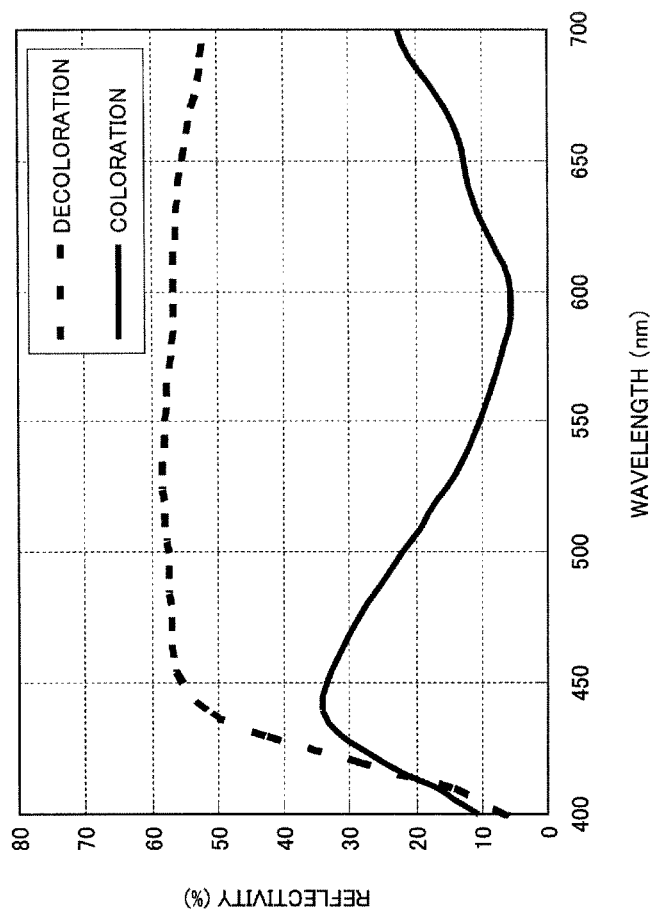
FIG. 4 is a spectral graph showing the reflectivity at coloration and decoloration of a display device based on test results of Example 8.
Figure 5:
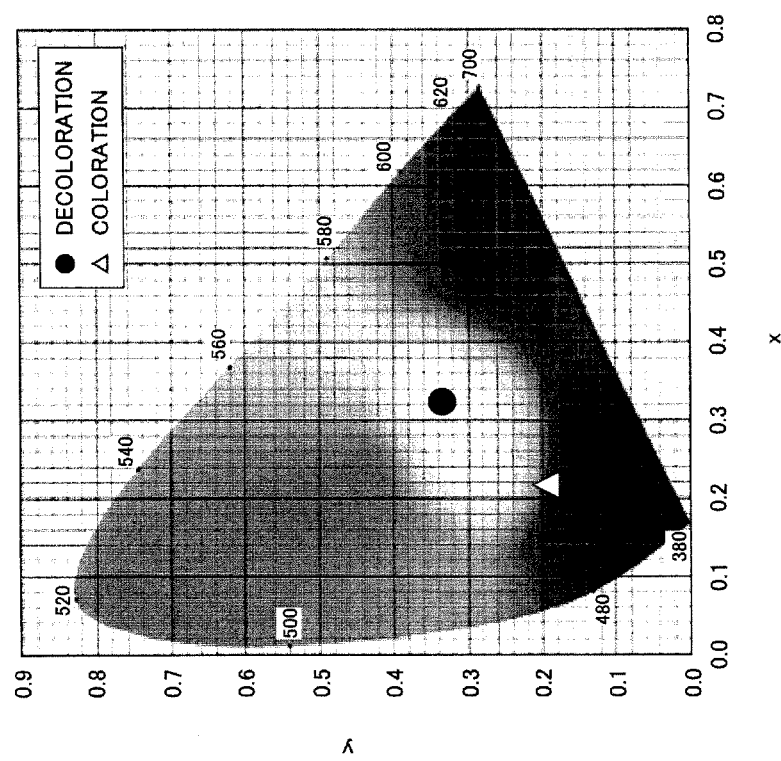
FIG. 5 is a graph showing coloration and decoloration color coordinates of the display device based on the test results of Example 8.

FIG. 4 is a spectral graph representing the reflectivity at coloration and decoloration of the display device. FIG. 5 shows the result of performing CIE color space conversion on the spectral graph of FIG. 4.

As can be appreciated from FIGS. 4 and 5, the electrochromic compound represented by Formula (11) synthesized in Example 1 is substantially colorless at decoloration and produces a clear cyan color upon coloration.

Next, the display electrode of the electrochromic display layer created in Example 7 was included in a quartz cell, a platinum electrode was used as an opposing electrode, an Ag/Ag+ electrode (RE-7 manufactured by BAS Inc.) was used as a reference electrode, and the cell was filled with an electrolyte solution prepared by adding 20 wt % of tetrabutylammonium perchlorate to dimethyl sulfoxide. This quartz cell was irradiated with deuterium tungsten halogen light (DH-2000 manufactured by Ocean Optics), the transmitted light was detected by a spectrometer (USB4000 manufactured by Ocean Optics), and the absorbance spectrum was measured.

Figure 6:
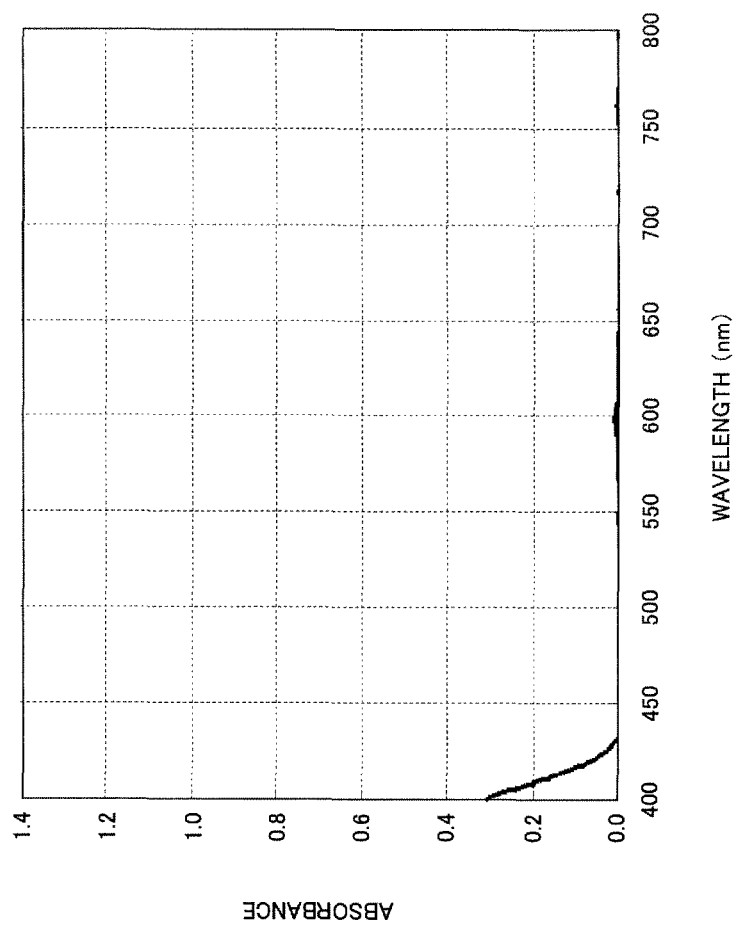
FIG. 6 shows an absorbance spectrum of the display device at decoloration based on the test results of Example 8.
Figure 7:
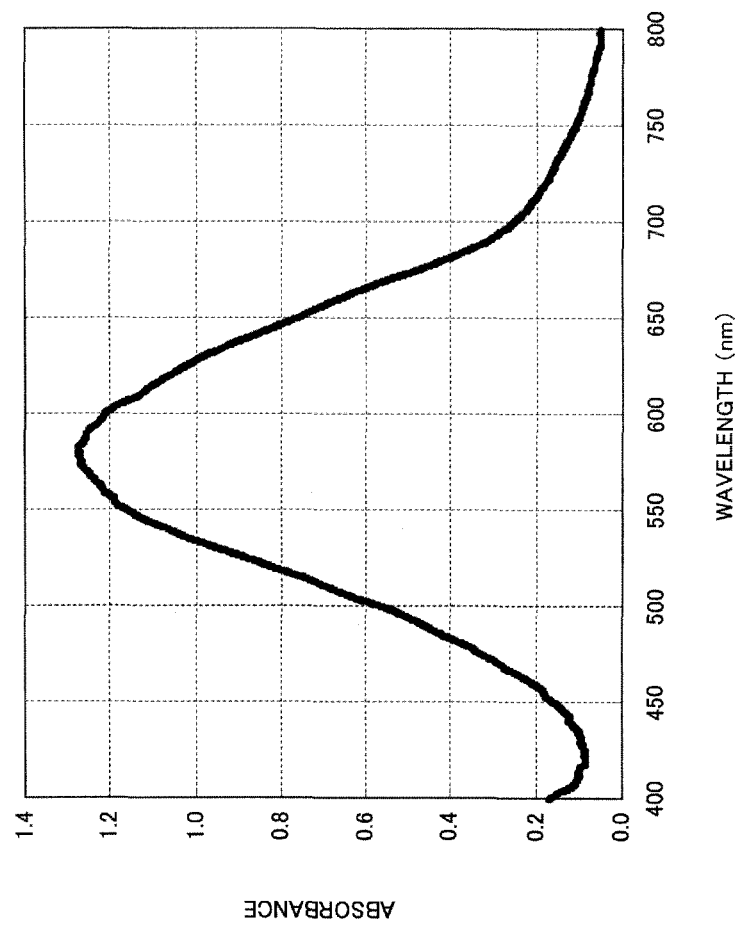
FIG. 7 shows an absorbance spectrum of the display device at coloration based on the test results of Example 8.

FIG. 6 shows the absorbance spectrum at decolorization before a voltage is applied. Upon applying a voltage of −1.5 V to the cell using a potentiostat (ALS-660C manufactured by BAS Inc.), the color cyan was produced with a maximum absorbance wavelength of 575 nm. FIG. 7 shows the absorbance spectrum of the cell at coloration.

Example 9

In Example 9, a color density retention test was conducted on electrochromic display devices.

Figure 8:
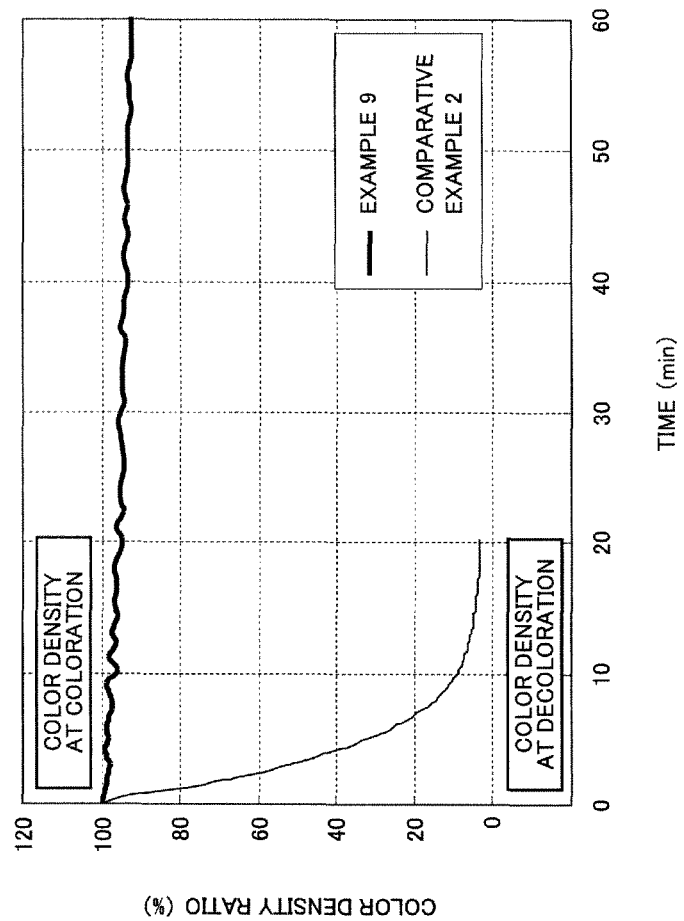
FIG. 8 is a correlation graph showing the color densities of display devices after an applied voltage is turned off.

Specifically, voltages were applied to the electrochromic display device manufactured in Example 7 and the electrochromic display device manufactured in Comparative Example 2 to induce coloration of the display devices, and after turning off the applied voltages, the decrease in color density of the display devices were observed. FIG. 8 shows a comparison of the color density decrease of the display devices in relation to the elapsed time after turning off the applied voltages where 100 represents the color density when the voltages are still applied.

As can be appreciated from FIG. 8, the electrochromic display device of Comparative Example 2 loses its color in approximately 10 minutes after the applied voltage is turned off, whereas the electrochromic display device of Example 7 retains 90% of its color density even after 1 hour elapses from the time the applied voltage is turned off. Further, even after 9 hours from the time the applied voltage is turned off, the electrochromic display device of Example 7 still retains 90% of its color density. That is, the electrochromic display device manufactured using an electrochromic display compound according to an embodiment of the present invention may achieve high color maintaining characteristics.

Example 10

Example 10 relates to an exemplary display device according to the second embodiment.

The electrochromic display device of Example 10 uses the electrochromic compound represented by Formula (13) synthesized in Example 2 and is manufactured in a manner identical to steps (a)-(c) of Example 7 for creating a display electrode, a display layer, and an electrochromic display device. Upon conducting a coloration/decoloration test on the electrochromic display device of Example 10 in a manner identical to Example 8, the color magenta was produced. Further, upon conducting a color density retention test on the electrochromic display device of Example 10 in a manner identical to Example 9, the electrochromic display device of Example 10 was able to maintain 90% of its color density even after 4 hours from the time an applied voltage was turned off.

Example 11

Example 11 relates to another exemplary electrochromic display device according to the second embodiment.

The electrochromic display device of Example 11 uses the electrochromic compound represented by Formula (3) synthesized in Example 3 and is manufactured in a manner identical to steps (a)-(c) of Example 7 for creating a display electrode, a display layer, and an electrochromic display device. Upon conducting a coloration/decoloration test on the electrochromic display device of Example 11 in a manner identical to Example 8, the color magenta was produced. Further, upon conducting a color density retention test on the electrochromic display device of Example 11 in a manner identical to Example 9, the electrochromic display device of Example 11 was able to maintain 90% of its color density even after 4 hours from the time an applied voltage was turned off.

Example 12

Example 12 relates to another exemplary electrochromic display device according to the second embodiment.

The electrochromic display device of Example 12 uses the electrochromic compound represented by Formula (23) synthesized in Example 4 and is manufactured in a manner identical to steps (a)-(c) of Example 7 for creating a display electrode, a display layer, and an electrochromic display device. Upon conducting a coloration/decoloration test on the electrochromic display device of Example 12 in a manner identical to Example 8, the color cyan was produced. Further, upon conducting a color density retention test on the electrochromic display device of Example 12 in a manner identical to Example 9, the electrochromic display device of Example 12 was able to maintain 90% of its color density even after 4 hours from the time an applied voltage was turned off.

Example 13

Example 13 relates to another exemplary electrochromic display device according to the second embodiment.

The electrochromic display device of Example 13 uses the electrochromic compound represented by Formula (29) synthesized in Example 5 and is manufactured in a manner identical to steps (a)-(c) of Example 7 for creating a display electrode, a display layer, and an electrochromic display device. Upon conducting a coloration/decoloration test on the electrochromic display device of Example 13 in a manner identical to Example B, the color magenta was produced. Further, upon conducting a color density retention test on the electrochromic display device of Example 13 in a manner identical to Example 9, the electrochromic display device of Example 13 was able to maintain 90% of its color density even after 4 hours from the time an applied voltage was turned off.

Example 14

Example 14 relates to another exemplary electrochromic display device according to the second embodiment.

The electrochromic display device of Example 14 uses the electrochromic compound represented by Formula (37) synthesized in Example 6 and is manufactured in a manner identical to steps (a)-(c) of Example 7 for creating a display electrode, a display layer, and an electrochromic display device. Upon conducting a coloration/decoloration test on the electrochromic display device of Example 14 in a manner identical to Example 8, the color magenta was produced. Further, upon conducting a color density retention test on the electrochromic display device of Example 14 in a manner identical to Example 9, the electrochromic display device of Example 14 was able to maintain 90% of its color density even after 4 hours from the time an applied voltage was turned off.

Example 15

Example 15 is an exemplary application of the first embodiment relating to the synthesis of the electrochromic compound represented by Formula (22). The electrochromic compound represented by Formula (22) may be synthesized by having the intermediate compound represented by Formula (11-1) of Example 1 react with a 2-equivalent amount of ethyl bromide.

Specifically, a solution of water/2,2,3,3-tetrafluoropropanol (10 wt %) is prepared, and the electrochromic compound represented by Formula (22) is dissolved at an amount equal to 1 wt % into this solution to create an electrochromic compound solution. Then, this electrochromic compound solution at an amount equal to 50 wt % is added to an electrolyte solution prepared by adding 20 wt % of tetrabutylammonium perchlorate to dimethyl sulfoxide. The resulting solution is enclosed within a cell that is created by bounding together two 30×30 mm glass substrates with $SnO_2$ conductive films (manufactured by AGC Fabritech Co., Ltd.) as the display substrate and the counter substrate via a spacer with a thickness of 75 µm to form the electrochromic display device 20.

Upon applying a voltage of 2.5 V for 2 seconds to the display device 20 manufactured in the above manner, the display device produced the color cyan. Upon applying a voltage of −1.5 V for 1 second, the color disappeared and the display device returned to a colorless transparent state.

Further, the present invention is not limited to these embodiments, and numerous variations and modifications may be made without departing from the scope of the present invention.

The present application is based on and claims the benefit of the priority dates of Japanese Patent Application Nos. 2011-259245 and 2012-184228 filed on Nov. 28, 2011 and Aug. 23, 2012, respectively, with the Japanese Patent Office, the entire contents of which are hereby incorporated by reference.

What is claimed is:

1. An electrochromic compound represented by the following General Formula (1)

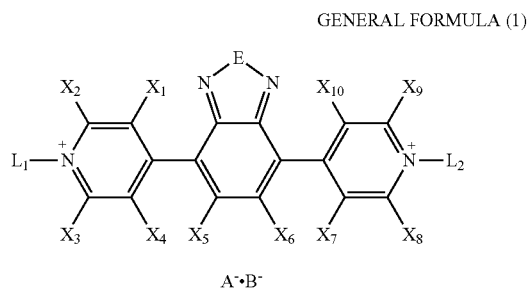

GENERAL FORMULA (1)

wherein E represents at least one of O, S, Se, and N—R; R represents at least one of a hydrogen atom, a substitutive aliphatic hydrocarbon group, and a substitutive aromatic hydrocarbon group; $X_1$-$X_{10}$ may be the same or different and each represent at least one of a hydrogen atom and a monovalent substituent; $L_1$ and $L_2$ may be the same or different and each represent a monovalent substituent; and $A^-$ and $B^-$ may be the same or different and each represent a monovalent anion.

2. The electrochromic compound as claimed in claim 1, wherein
at least one of $L_1$ and $L_2$ represents a functional group that is capable of directly or indirectly bonding with a hydroxyl group.

3. An electrochromic composition comprising:
a conductive or semi-conductive nanostructure; and
an electrochromic compound that is bound or adsorbed to the nanostructure, the electrochromic compound being represented by the following General Formula (1)

GENERAL FORMULA (1)

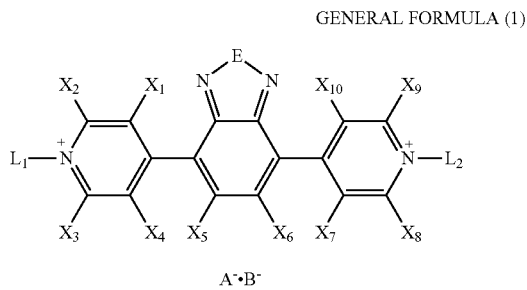

A⁻·B⁻ wherein E represents at least one of O, S, Se, and N—R; R represents at least one of a hydrogen atom, a substitutive aliphatic hydrocarbon group, and a substitutive aromatic hydrocarbon group; $X_1$-$X_{10}$ may be the same or different and each represent at least one of a hydrogen atom and a monovalent substituent; $L_1$ and $L_2$ may be the same or different and each represent a monovalent substituent; and A⁻ and B⁻ may be the same or different and each represent a monovalent anion.

4. A display device comprising:
a display electrode;
a counter electrode arranged opposite the display electrode at a predetermined distance from the display electrode;
an electrolyte arranged between the display electrode and the counter electrode; and
a display layer arranged on a surface of the display electrode facing towards the counter electrode, the display layer including an electrochromic compound represented by the following General Formula (1)

GENERAL FORMULA (1)

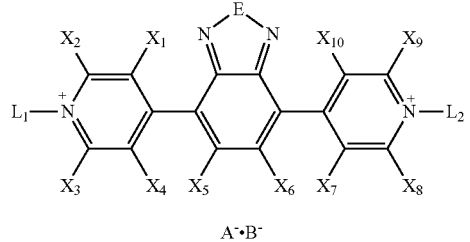

A⁻·B⁻ wherein E represents at least one of O, S, Se, and N—R; R represents at least one of a hydrogen atom, a substitutive aliphatic hydrocarbon group, and a substitutive aromatic hydrocarbon group; $X_1$-$X_{10}$ may be the same or different and each represent at least one of a hydrogen atom and a monovalent substituent; $L_1$ and $L_2$ may be the same or different and each represent a monovalent substituent; and A⁻ and B⁻ may be the same or different and each represent a monovalent anion.

5. The display device as claimed in claim 4, wherein the display layer includes an electrochromic composition including a conductive or semi-conductive nanostructure and the electrochromic compound that is bound or adsorbed to the nanostructure.

6. The display device as claimed in claim 4, further comprising:
a white reflective layer arranged on a surface of the counter electrode facing the display electrode.

7. The display device as claimed in claim 4, wherein the display electrode includes a transparent conductive film.

* * * * *